US009754185B2

United States Patent
Ikeda et al.

(10) Patent No.: US 9,754,185 B2
(45) Date of Patent: Sep. 5, 2017

(54) ULTRASOUND IMAGING APPARATUS

(75) Inventors: Teiichiro Ikeda, Tokyo (JP); Takashi Azuma, Tokyo (JP); Hiroshi Masuzawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 540 days.

(21) Appl. No.: 14/342,101

(22) PCT Filed: Aug. 7, 2012

(86) PCT No.: PCT/JP2012/070113
§ 371 (c)(1),
(2), (4) Date: Apr. 1, 2014

(87) PCT Pub. No.: WO2013/038847
PCT Pub. Date: Mar. 21, 2013

(65) Prior Publication Data
US 2014/0240482 A1  Aug. 28, 2014

(30) Foreign Application Priority Data

Sep. 15, 2011  (JP) .................................. 2011-202342

(51) Int. Cl.
*H04N 5/00* (2011.01)
*G06K 9/62* (2006.01)
(Continued)

(52) U.S. Cl.
CPC .......... *G06K 9/6202* (2013.01); *A61B 8/5207* (2013.01); *G01S 7/52047* (2013.01);
(Continued)

(58) Field of Classification Search
CPC . G01S 15/00; G01S 15/89; G01S 7/52; G01S 7/52046; G01S 15/8927;
(Continued)

(56) References Cited

U.S. PATENT DOCUMENTS 6,193,659 B1 * 2/2001 Ramamurthy ......... A61B 8/481
                                                     600/443
6,482,160 B1 * 11/2002 Stergiopoulos ..... G01S 7/52046
                                                     128/916
(Continued)

FOREIGN PATENT DOCUMENTS

JP        07-303640 A    11/1995
JP        11-235341 A    8/1999
JP        2001-187055 A  7/2001

OTHER PUBLICATIONS

B. Mohammadzadeh, "Minimum Variance Beamforming Combined with Adaptive Coherence Weighting Applied to Medical Ultrasound Imaging" IEEE Transaction on Ultrasonics, Ferroelectircs and Frequency Control, vol. 5, No. 9, Sep. 2009, pp. 1923-1931.
(Continued)

*Primary Examiner* — Frank Huang
(74) *Attorney, Agent, or Firm* — Brundidge & Stanger, P.C.

(57) ABSTRACT

A weight value used for a beamforming process performed on received signals in an ultrasound imaging apparatus is obtained with a small amount of computations and with a high degree of precision, even when a method of adaptive signal processing is employed.

Multiple elements 401 receive ultrasound signals from a test subject, and the similarity operator 404 obtains the similarity between the received signals x(n). By using the similarity C(n) between the received signals obtained by the similarity operator 404, the adaptive weight operator 407 computes the adaptive weight w(n) in association with the similarity. The beamforming operator 408 uses the adaptive weight w(n) and the received signal x(n) to generate a beamforming output. The imaging processor 108 uses the beamforming
(Continued)

output to generate image data. By way of example, the similarity operator 404 performs computations of the similarity in the time direction.

16 Claims, 17 Drawing Sheets

(51) Int. Cl.
   *A61B 8/08*     (2006.01)
   *G01S 7/52*     (2006.01)
   *G06T 7/00*     (2017.01)
   *H04N 5/232*    (2006.01)
   *G10K 11/34*    (2006.01)
   *A61B 8/00*     (2006.01)
   *G01S 15/89*    (2006.01)

(52) U.S. Cl.
   CPC ........ G01S 15/8915 (2013.01); G06T 7/0012 (2013.01); G10K 11/346 (2013.01); H04N 5/232 (2013.01); *A61B 8/4405* (2013.01); *A61B 8/461* (2013.01); *A61B 8/467* (2013.01); *G01S 15/8927* (2013.01)

(58) Field of Classification Search
   CPC ............. G01S 15/8993; G01S 7/52047; G01S 15/8929; G10K 11/00; G10K 11/34; G10K 11/346; G10K 11/10; Y10S 128/916; A61B 8/5269; H01Q 3/22
   See application file for complete search history.

(56) References Cited

U.S. PATENT DOCUMENTS

| | | | | |
|---|---|---|---|---|
| 6,719,696 B2* | 4/2004 | Stergiopoulos | ..... | G01S 7/52046 128/916 |
| 7,280,627 B2* | 10/2007 | Orlin | .................... | H01Q 3/2611 375/347 |
| 7,867,166 B2* | 1/2011 | Waag | ................. | G01S 7/52049 600/437 |
| 7,887,486 B2* | 2/2011 | Ustuner | ............... | A61B 8/5269 600/437 |
| 7,914,454 B2* | 3/2011 | Weber | .................... | A61B 8/483 600/407 |
| 8,007,439 B2* | 8/2011 | Specht | ..................... | A61B 8/42 600/437 |
| 8,968,205 B2* | 3/2015 | Zeng | ........................ | A61N 7/02 367/103 |
| 2003/0065262 A1* | 4/2003 | Stergiopoulos | ..... | G01S 7/52046 600/437 |
| 2005/0033165 A1* | 2/2005 | Ustuner | ............... | A61B 8/5269 600/437 |
| 2005/0073457 A1* | 4/2005 | Li | ............................ | H01Q 3/22 342/368 |

OTHER PUBLICATIONS

J.F. Synnevag, "Speckle Statistics in Adaptive Beamforming", 2007 IEEE Ultrasonics Symposium, Oct. 2007, pp. 1545-1548.

International Search Report from International Application No. PCT/JP201/070113 mailed Oct. 23, 2012.

International Preliminary Report on Patentability in corresponding application No. PCT/JP2012/070113 reported on Mar. 18, 2014.

* cited by examiner $$y(n) = \sum_{k=1}^{K} w^* x_k(n - \Delta t_k(n))$$

FIG.12
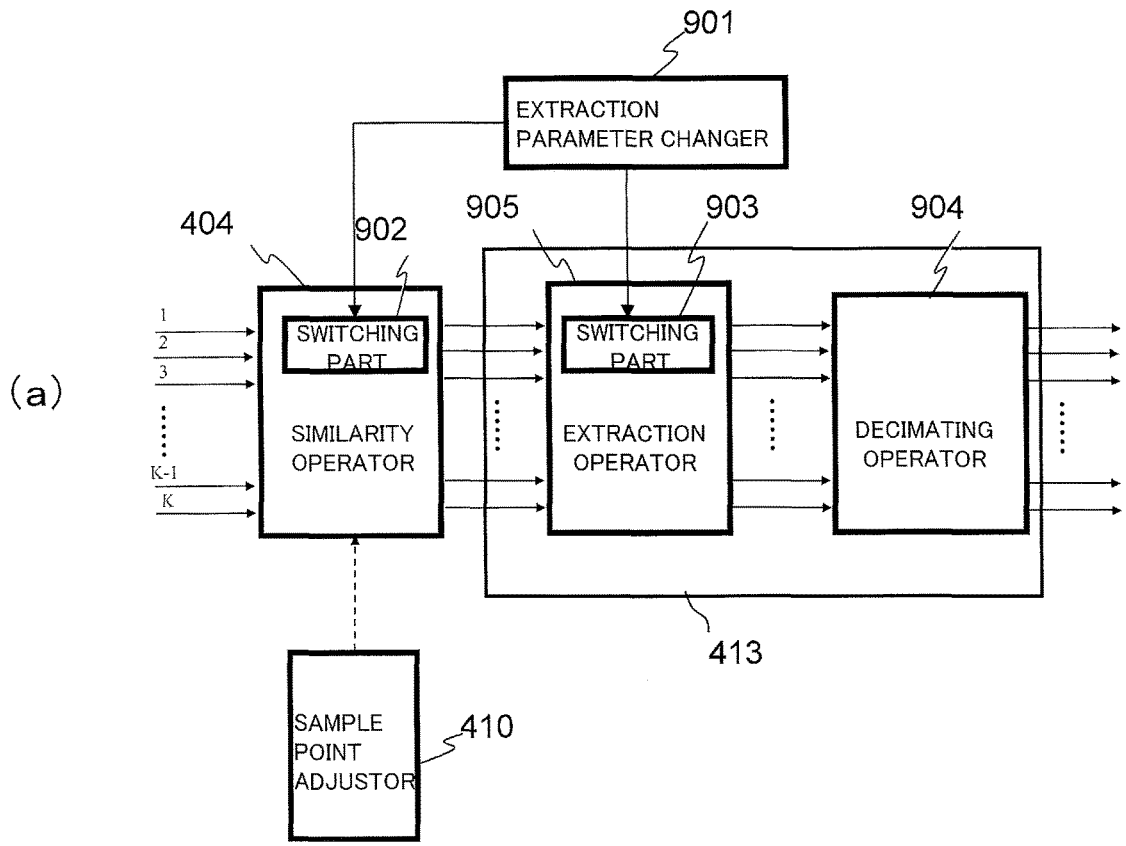
(a)
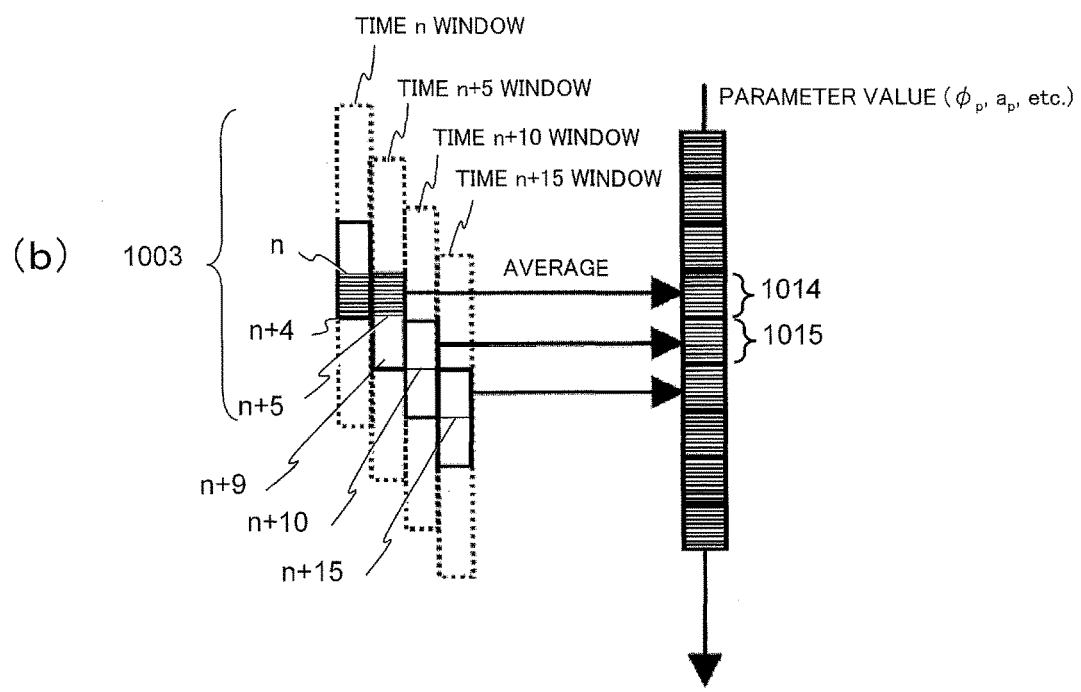
(b)

FIG.15
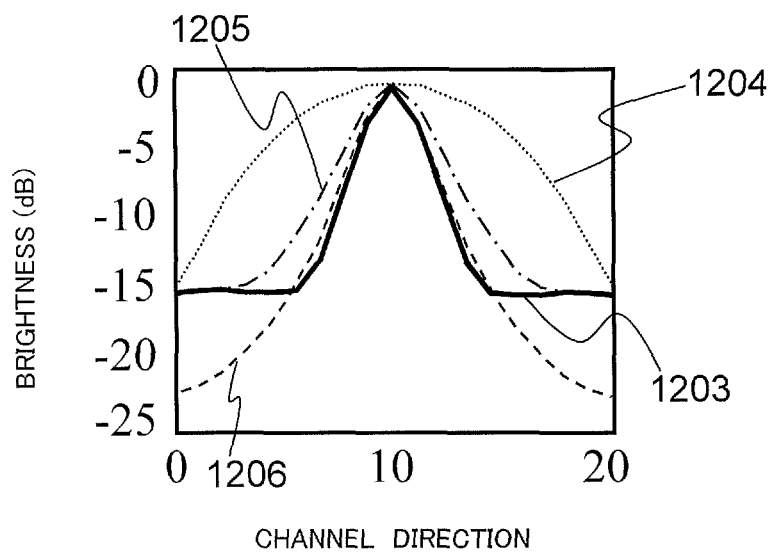
(a)
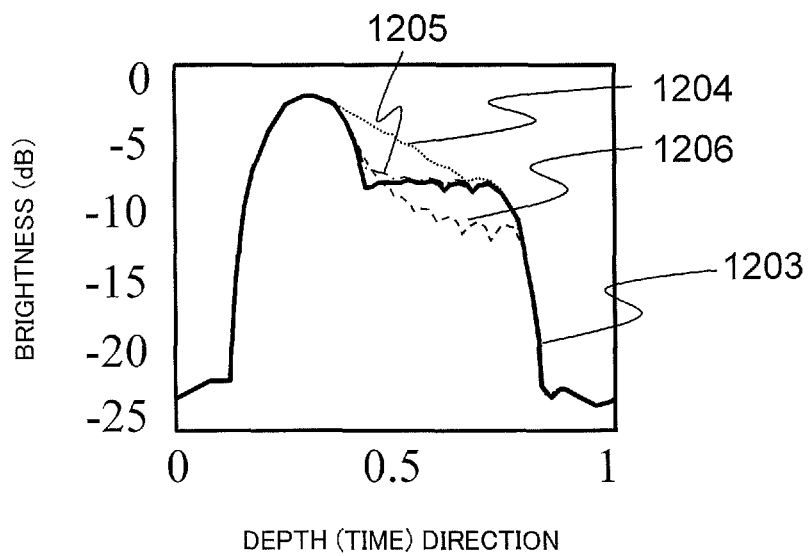
(b)

ULTRASOUND IMAGING APPARATUS

TECHNICAL FIELD

The present invention relates to an ultrasound imaging technique for taking an image within a test subject, through the use of ultrasound wave.

BACKGROUND ART

Ultrasound imaging is a technique for non-invasively creating an image of the inside of a test subject including a human body, through the use of ultrasound wave (sound wave not intended for hearing, and generally high-frequency sound wave having 20 kHz or higher). By way of example, a medical ultrasound imaging apparatus will be briefly explained. An ultrasound probe transmits the ultrasound waves to the inside of a patient, and receives echo signals reflected from the inside of the patient.

The received signals are subjected to signal processing in one or both of the ultrasound probe and the main unit of the ultrasound imaging apparatus, and thereafter transferred to a monitor and an ultrasound image is displayed thereon. More specifically, for example, a transmit beamformer in the main unit of the ultrasound imaging apparatus generates signals of a transmission beam, allowing the signals to pass through the transmit-receive separation circuit, and thereafter transfers the signals to the ultrasound probe. The ultrasound probe sends out the ultrasound waves. After receiving echo signals from the internal body, the ultrasound probe transmits the signals to the main unit of the imaging apparatus. In the main unit of the imaging apparatus, the received signals pass through the transmit-receive separation circuit and the receive beamformer, and those signals are transmitted to an image processor. The image processor executes various imaging processes using various filters, a scan converter, and the like. Finally, the monitor displays an ultrasound image.

As described above, a general ultrasound diagnostic apparatus is made up of three techniques; transmit beamforming, receive beamforming, and a backend imaging processing. Particularly, since the beamformers for transmitting and receiving perform signal processing at an RF (high-frequency) level, algorithms and implementation architecture in the beamformers decide a basic image quality of the ultrasound image. Therefore, the beamformers serve as major parts of the apparatus.

The receive beamformer assigns a delay time to each received signal (received data) in multiple elements that constitute the ultrasound probe, the delay time distributing an amount of delay in a concave form, in association with the relations between a focal position and the element positions, and after virtually obtaining the focal point (focused) at a certain point in space, the received signal data items are summed up. This method is referred to as a beamforming according to a delay-and-sum method. In this delay-and-sum method, the received data items that are received by the multiple elements in the ultrasound diagnostic apparatus are multiplied by a fixed weight vector stored in the diagnostic apparatus, and the delay is implemented according to this processing means. This process is also performed in the transmit beamformer in a similar manner, not only in the receive beamformer.

On the other hand, as a basic problem of the ultrasound imaging apparatus, it is known that lateral resolution is subject to constraints. Since transmitting and receiving of the ultrasound waves are performed by an array having a finite opening size, there is an impact of diffraction at the edge of the opening. If an infinitely long array is prepared, there is a possibility that the resolution is enhanced infinitely in the same manner as in the depth direction. In actual, however, a physical restriction in designing the apparatus, i.e., the length of the array, has hampered the enhancement of the lateral resolution. In recent years, it is attempted that the aforementioned fixed weight vector used for delaying, upon summing of delays by the beamformer, is changed adaptively for the time-series transmit-receive data items, one by one, thereby obtaining an ultrasound image of higher definition, and this attempt is coming to attention. Accordingly, there is a possibility that this brings a marked improvement in the lateral resolution, being one of essential problems in the beamforming technique.

Particularly in recent years, the patent document 1, for example, discloses that an adaptive signal processing technique including the MVDR method (Minimum Variance Distortionless Response; Capon method) that has been developed in the field of mobile communication is applied to the ultrasound imaging process. By using the adaptive method, the weight vector being a fixed value conventionally, is obtained for each sample point of the received signal in the time direction, and the received signal is multiplied by this weight vector, thereby achieving delay.

PRIOR ART DOCUMENT

Patent Document

Patent Document 1
U.S. Unexamined patent application Publication Ser. No. 10/676,777 Specification

DISCLOSURE OF THE INVENTION

Problem to be Solved by the Invention

Upon employing the technique (adaptive beamformer) for applying the adaptive signal processing technique such as the MVDR method to a beamformer, if a correlation matrix in the spatial direction (e.g. spatial covariance matrix) is calculated sequentially (every sample and every channel), without performing estimation in the time direction, it may become difficult to converge errors in energy that has been dispersed in the time direction. Therefore, a point image within the image may become blurred in the time direction (depth direction), and instability may occur in the processing against various noise, thereby causing an image noise error.

On the other hand, in the case where both estimation in the time direction and estimation in the spatial direction are performed according to the adaptive signal processing, this may cause enormous processing loads, and implementation cost is greatly increased. Such a trade-off between the throughput capacity and burdens in the estimating process becomes a large obstacle for the implementation.

An object of the present invention is to obtain a weight value that is used in the beamforming process performed on the received signals in the ultrasound imaging apparatus, according to a small amount of computations with a high degree of precision, even when the adaptive signal processing is employed.

Means to Solve the Problem

In order to achieve the above object, the present invention provides the ultrasound imaging apparatus as described below. In other words, it is directed to the ultrasound imaging apparatus having multiple elements for receiving ultrasound signals from a test subject, a similarity operator for obtaining similarity between the received signals of the multiple elements, an adaptive weight operator for obtaining an adaptive weight associated with the similarity by using the similarity between the received signals obtained by the similarity operator, a beamforming operator for generating a beamforming output by using the adaptive weight and the received signal, and an image processor for generating image data by using the beamforming output.

Effect of the Invention

In the present invention, a process for computing the similarity is performed in advance as to the received signals, and an adaptive weight is computed by using thus obtained similarity, thereby reducing the amount of computations and achieving an accurate estimation of an point image. For example, by performing the process for computing the similarity in the time direction, it is possible to correct fluctuations in the time direction according to a relatively small amount of computations, and perform estimation of more accurate point image. With the configuration above, image blurring in the time direction (depth direction) is corrected, enabling acquisition of the point image being small in diameter, and allowing acquisition of an ultrasound image including little false images and noise in stable manner.

BRIEF DESCRIPTION OF DRAWINGS

FIG. 12(a) is a block diagram illustrating a partial configuration of the receive beamformer according to the sixth embodiment, and FIG. 12(b) illustrates a decimation process;

FIG. 15 (a) is a graph obtained by profiling along the channel direction, the brightness at the depth where the maximum brightness point exists, in the ultrasound images as shown in FIG. 14(a) to FIG. 14(d), and FIG. 15 (b) is a graph obtained by profiling along the depth direction, the brightness at the channel where the maximum brightness point exists, in the ultrasound images as shown in FIG. 14(a) to FIG. 14(d);

BEST MODE FOR CARRYING OUT THE INVENTION

Figure 1:
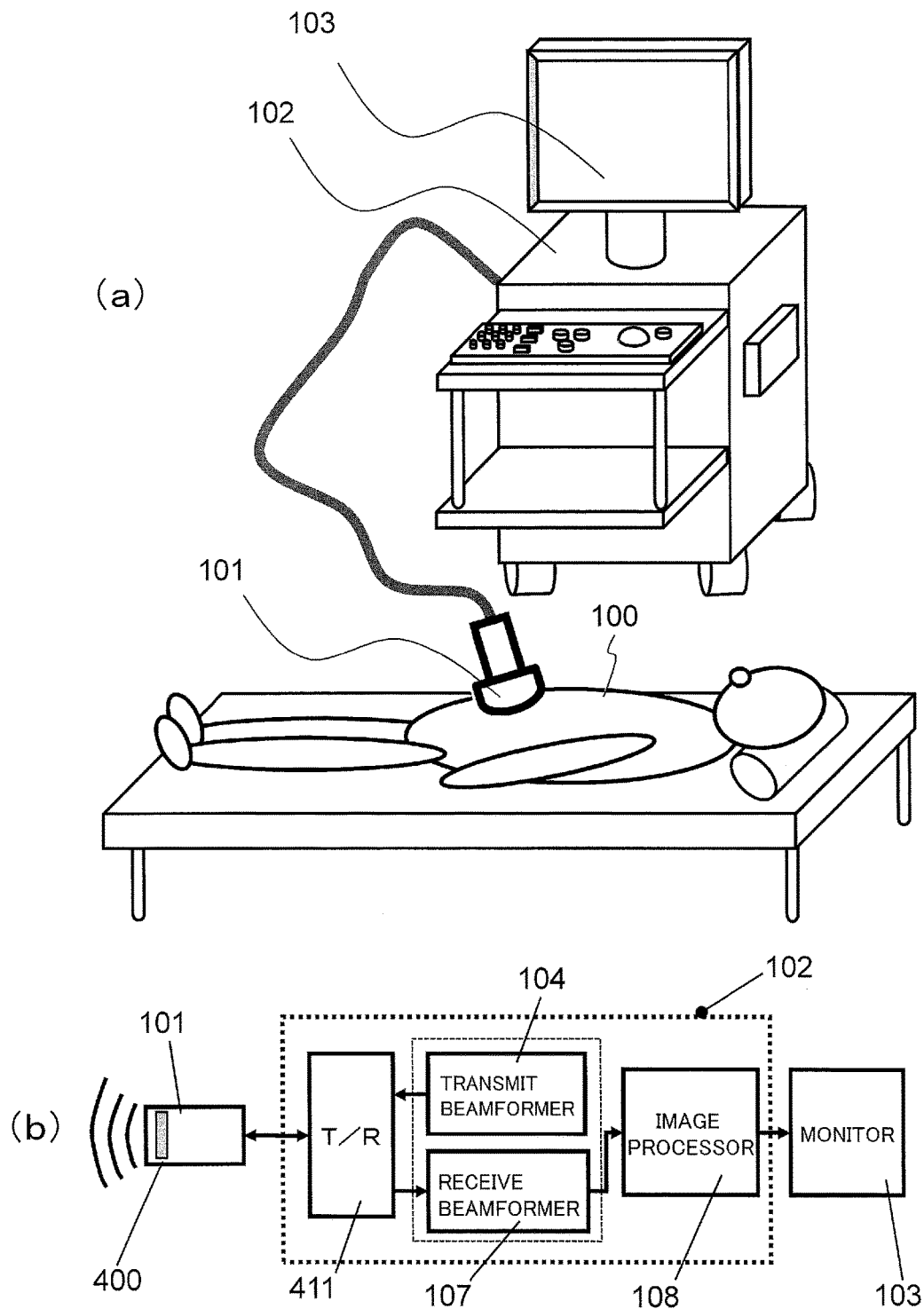
FIG. 1(a) is a perspective view illustrating a schematic configuration of the ultrasound imaging apparatus according to the present embodiment.
FIG. 1(b) is a block diagram thereof.

According to a first aspect of the present invention, the ultrasound imaging apparatus as described in the following is provided. That is, the first aspect of the present invention is directed to the ultrasound imaging apparatus having multiple elements for receiving ultrasound signals from a test subject, a similarity operator for obtaining similarity between the received signals of the multiple elements, an adaptive weight operator for obtaining an adaptive weight associated with the similarity, by using the similarity between the received signals obtained by the similarity operator, a beamforming operator for generating a beamforming output by using the adaptive weight and the received signal, and an image processor for generating image data by using the beamforming output. With the configuration as described above, it is possible to obtain a weight value used for the beamforming process performed on the received signal in the ultrasound imaging apparatus, with a small amount of computations and with a high degree of precision, even when a method of the adaptive signal processing is employed.

Preferably, the direction along which the similarity operator performs the similarity computation is a time direction.

By way of example, the adaptive weight operator may be configured as performing the adaptive signal processing, through the use of the similarity that is obtained by the similarity operator, so as to obtain the adaptive weight.

Preferably, a delay part may be placed between the multiple elements and the similarity operator, so as to delay each of the signals being received by the multiple elements, in association with a focal position of the ultrasound signals, and to align the wave fronts. This configuration allows the similarity operator to obtain the similarity of the received signals being delayed by the delay part.

By way of example, it is configured such that an extractor is placed between the similarity operator and the adaptive weight operator, the extractor extracting a predetermined index value indicating the characteristics of the similarity, and the adaptive weight operator uses as the similarity, the index value that is extracted by the extractor.

The adaptive weight operator has a configuration to generate a spatial covariance matrix from the similarity between the received signals, for instance, performs the adaptive signal processing to obtain the adaptive weight.

Multiple elements for receiving the ultrasound signals may be placed side by side. On this occasion, the similarity operator is configured as obtaining the similarity between the received signals of two elements out of the multiple elements, one of the two elements being positioned, a predetermined number of the elements away from the other element.

If the number of the adaptive weights obtained by the adaptive weight operator is less than the number of the received signals, the beamforming operator may perform computations to allow the multiple received signals to degenerate in accordance with the number of the adaptive weights, and generate a beamforming output through the use of the received signals after degeneration and the adaptive weights.

According to the second aspect of the present invention, the ultrasound imaging apparatus as described below is provided. In other words, it is directed to the ultrasound imaging apparatus having multiple elements for receiving ultrasound signals from a test subject, a similarity operator for obtaining similarity between the received signals of the multiple elements, an adaptive weight operator for obtaining an adaptive weight associated with the similarity by using the similarity between the received signals obtained by the similarity operator, a beamforming operator for generating a beamforming output by using the adaptive weight and the received signal, and an image processor for generating image data by using the beamforming output. The ultrasound imaging apparatus in this aspect of the invention obtains a weight value used for the beamforming process performed on the received signal in the ultrasound imaging apparatus with a small amount of computations and with a high degree of precision, even when a method of the adaptive signal processing is employed.

In the aforementioned second aspect of the invention, it is possible to arrange between the similarity operator and the adaptive weight operator, an extractor for extracting a predetermined index value indicating characteristics of the similarity, and a delay part for delaying each of the received signals of the multiple elements based on the index value that is extracted by the extractor, and aligning the wave fronts. In this case, the adaptive weight operator is allowed to obtain the adaptive weight by using the received signal being delayed by the delay part.

As discussed above, in the present invention, similarity computation is performed in advance as to the received signal, and thus obtained similarity or the received signal delayed in advance by the obtained similarity is used to compute the adaptive weight, thereby reducing the amount of computations and allowing estimation of an accurate point image. By way of example, the process for computing the similarity in the time direction may correct the fluctuations in the time direction by relatively a small amount of computations and allowing more accurate estimation of the point image. This configuration corrects the image blurring in the time direction (depth direction) and a point image being small in diameter is able to be obtained, achieving stable acquisition of an ultrasound image from which false images and noise are reduced.

One embodiment of the present invention will be explained as a specific example.

First Embodiment

The ultrasound imaging apparatus according to the first aspect of the present invention as described above will be specifically explained as the first embodiment.

Firstly, with reference to FIG. 1(a) and FIG. 1(b), the entire configuration of the ultrasound imaging apparatus will be explained. FIG. 1(a) is a perspective view of the apparatus, and FIG. 1(b) is a block diagram illustrating a schematic configuration of the inside thereof.

As illustrated in FIG. 1(a), the ultrasound imaging apparatus is provided with the ultrasound probe 101, the apparatus main body 102, and the monitor 103. As illustrated in FIG. 1(b), there are arranged in the apparatus main body 102, the transmit beamformer 104, the transmit-receive separation circuit 411, the receive beamformer 107, and the image processor 108.

The transmit beamformer 104 generates signals of a transmission beam, allowing the signals to pass through the transmit-receive separation circuit 411, and thereafter transfers the signals to the ultrasound probe 101. The ultrasound probe 101 transmits the ultrasound waves toward the internal body of the test subject 100, and the ultrasound probe 101 receives echo signals reflected inside the body. The received signals pass through the transmit-receive separation circuit 411 and are subjected to beamforming computation process, and the like, in the receive beamformer 107. The received signals after the beamforming computation are transferred to the image processor 108, and various imaging processes are executed, using various filters, a scan converter, and the like, thereby generating an ultrasound image. The ultrasound image is transferred to the monitor 103, and displayed thereon.

Figure 2:
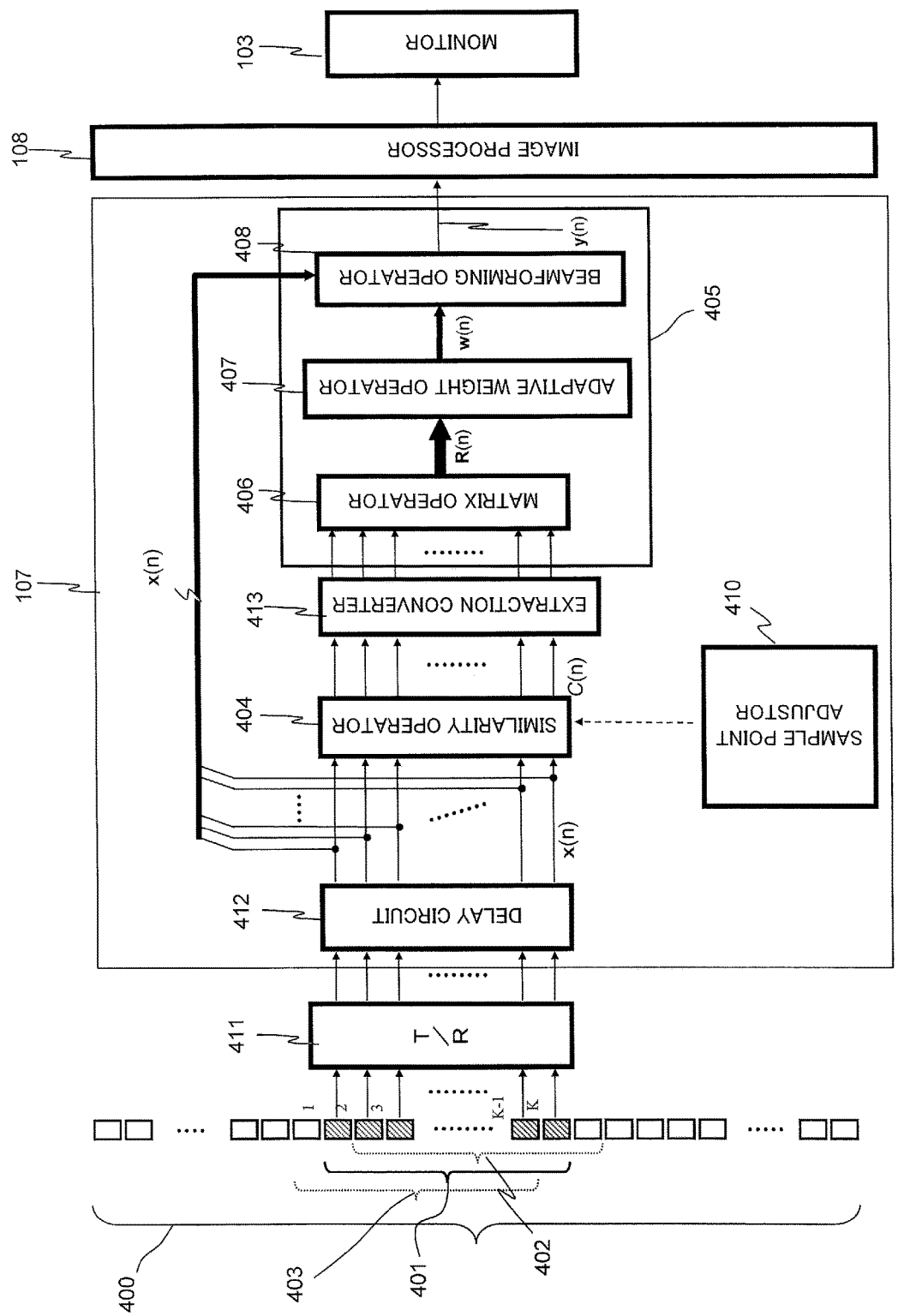
FIG. 2 is a block diagram illustrating a configuration of the receive beamformer according to a first embodiment.

FIG. 2 is a block diagram illustrating a configuration of the receive beamformer 107. This receive beamformer is an adaptive beamformer in which a technique of adaptive signal processing is applied to the beamformer. As shown in FIG. 2, the receive beamformer 107 incorporates a delay circuit 412, the similarity operator 404, a sample point adjuster 410, an extraction converter 413, and an adaptive beamforming engine 405. Those components of the receive beamformer 107 may be configured as independent circuit, respectively. As an alternative configuration, operations of those components may be implemented, according to a memory for storing programs in advance, and a CPU and a GPU for reading and executing those programs.

The similarity operator 404 obtains according to computations, similarity in the time direction between received data items of multiple elements constituting the ultrasound probe 101 (hereinafter, also referred to as "received data"), and inputs information being calculated based on the computation result, in the adaptive beamforming engine 405. Processing for computing the similarity in the time direction in advance allows the adaptive beamforming engine 405 to correct fluctuations in the time direction with a relatively small amount of computations, enabling more accurate estimation of a point image. It is to be noted that as a previous stage of the similarity operator 404, the delay circuit 412 is arranged to provide a delay time depending on the position of the elements, to the received signals respectively of the multiple elements constituting the ultrasound probe, and perform processing for virtually obtaining a focal point (focused) at a certain point in the space.

The ultrasound probe 101 is provided with multiple elements (ultrasound wave transducers) 400 arranged in an array. The present embodiment employs an active channel technique, the elements in a partial region of the elements 400 are assumed as the active channels 401, in the ultrasound probe 101 that has received echoes in response to one transmit ultrasound beam, and by using the received signals in the active channels 401, one image data (one raster) in the direction along which the ultrasound wave propagates is generated. As illustrated in FIG. 2, multiple active channels 402, 401, and 403 are sequentially structured, while shifting the positions of the elements gradually, rasters are generated respectively for the active channels 402, 401, and 403, and those results are arranged to produce an ultrasound image.

Figure 3:
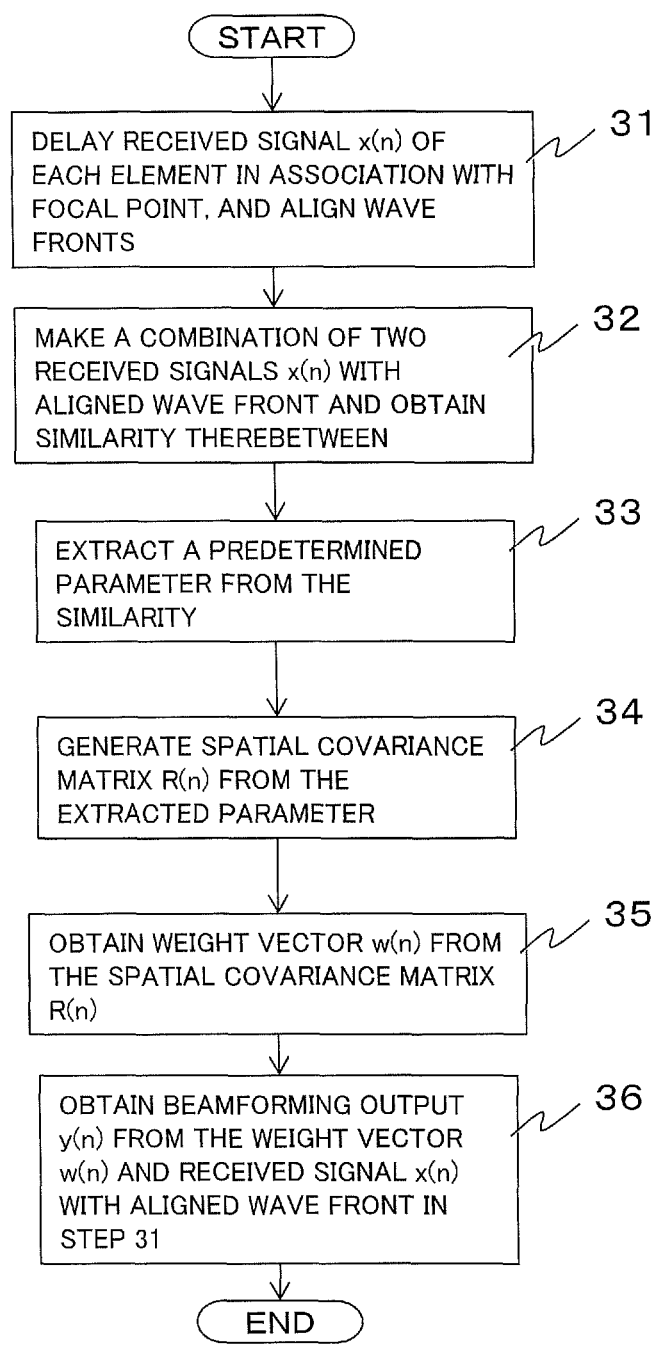
FIG. 3 is a flowchart showing a signal processing of the receive beamformer according to the first embodiment.

In the following, operations of each component will be explained, in the case where the received data on each of the elements in one active channel 401 in association with one transmitting-receiving, is subjected to the adaptive beamforming process, thereby generating one raster. FIG. 3 is a flow illustrating the processing of the receive beamformer for this case.

The multiple data items received by the active channel 401 pass through the transmit-receive separation circuit 411, and are inputted in the delay circuit 412 of the receive beamformer 107.

Figure 4:
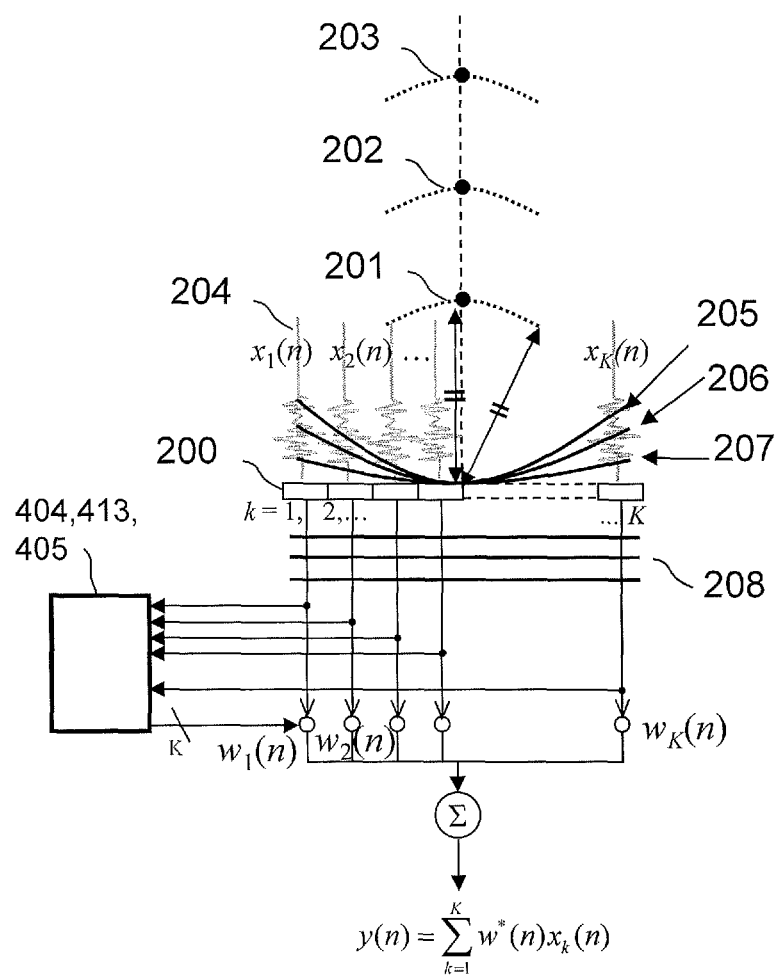
FIG. 4 illustrates operations of the receive beamformer according to the first embodiment.

In the step 31, as shown in FIG. 4, the delay circuit 412 provides a delay time to each received signal (received data) in the multiple elements 400 constituting the active channel 401, depending on the positions of the elements, the delay time distributing an amount of delay in a concave form 205 centering on one point 201 in the space and virtually focusing on the focal point 201 (step 31). By changing the shape of the concave form 205 to the concave forms 206 and 207, for instance, it is possible to allow the focal point to focus on the points 202 and 203, respectively. This configuration enables delaying of the received signal 204 of each of the elements 400 in accordance with a desired focal point, thereby obtaining the received signals (received data) 208 in which the wave fronts 1000 are aligned.

As shown in FIG. 5(a), if the number of the elements (channel count) constituting the active channel 401 is K, the received data 208 at a certain sample point of time n is expressed by the following vector x(n) as shown in the following formula (1):

[Formula 1]

$$x(n)=[x_1(n),x_2(n), \ldots ,x_K(n)]^T \quad (1)$$

In the step 32, the similarity operator 404 placed in the stage subsequent to the delay circuit 412 receives as an input signal, the vector x(n) made up of K received data items from the delay circuit 412, and performs the similarity computation between the received signals of the different channels (elements). Specifically, the similarity operator 404 calculates a similarity function between the channels of the active channel (total count K), and outputs a result of the calculation. As the similarity function, any function may be employed for outputting the similarity between multiple signal vectors, such as Mahalanobis' generalized distance, Pearson similarity function, and a cross correlation function.

Here, as an example of the similarity computation, the computation employing the cross correlation function will be explained. The cross correlation function is one of the methods for representing the similarity between a signal and another signal, and generally, it is expressed by the function $C_p(n)$ as shown in the following formula (2). As shown in the formula (2), the cross correlation function $C_p(n)$ is expressed as a convolution between the received data $x_p(n)$ of a certain channel p, and the signal $x^*_{p+q}(n+\tau)$ that is obtained by flipping only by $\tau$ in the time direction, the received data $x_{p+q}(n)$ of the channel p+q being q channels away from the channel p, and taking a conjugate thereof. Here, it may be configured optionally how many channels exist from the channel p to the channel p+q, and q is any value as far as it satisfies the formula (3). By way of example, if q=1, $C_p(n)$ represents the cross correlation function between the adjacent channels. When the total number of channels is K, as expressed by the formula (4), (K−q) cross correlation functions are outputted. For example, when q=3, correlation is taken with the channel three channels away, and cross correlation functions $C_1(n)$ to $C_{K-q}(n)$ of (K−3) combinations are outputted, i.e., (ch.1, ch.4), (ch2, ch5) . . . (ch.K−3, ch.K) in total. In the formula (2), the integral interval from −r to r indicates an interval in a cross correlation window 1003 as shown in FIG. 5(a), and the computation as shown in the formula (2) is performed as to the received data x(n) at each sample point of time within the cross correlation window 1003.

[Formula 2]

$$C_p(n)=\int_{-r}^{r} xhd\ p(n)x^*_{p+q}(n+\tau)d\tau \quad (2)$$

[Formula 3]

$$1 \le q \le K-2 \quad (3)$$

[Formula 4]

$$1 \le p \le K-q \quad (4)$$

FIG. 5(b) illustrates the cross correlation functions $C_1(n)$ to $C_{K-q}(n)$ obtained according to the formula (2). It is to be noted here that FIG. 5(b) illustrates the case where q=1.

The size of the cross correlation window 1003 may be a predetermined fixed value. Alternatively, the sample point adjuster 410 may be configured as setting any size in response to an instruction from an operator. Specifically, in the formula (2), by changing the size of the integral interval r, the size of the cross correlation window 1003 may also be changed. In other words, the sample point adjuster 410 functions as a window-length adjuster for setting any length of window in the time direction of the received signals.

The (K−q) cross correlation functions $C_1(n)$ to $C_{K-q}(n)$ calculated according to the formula (2) are transferred to extraction converter 413. In the step 33, as shown in the formula (5) and the formula (6), the extraction converter 413 extracts a value of one or more predetermined index (parameter) indicating the characteristics of the cross correlation function $C_p(n)$. The parameter value is extracted for each of the (K−q) cross correlation functions $C_1(n)$ to $C_{K-q}(n)$. As the parameter, at least one parameter among the following is used; maximum value (peak amplitude) $a_p$ of $C_p(n)$ in the time direction, time lag $\Delta t_p(n)$ at the point of time taking the maximum value $a_p$ from the reference point of time $t_0$, $\phi_p(n)$ obtained by converting $\Delta t_p(n)$ to phase, complex number (complex data) $\xi_p(n)$ expressed by the maximum value $a_p$ and $\phi_p(n)$ as indicated in the formula (7), a combination of complex components $I_p$ and $q_p$ as indicated in the formula (8), and only the real part or only the imaginary part of the complex components.

The value of the predetermined parameter extracted by the extraction converter 413 is inputted into the adaptive beamforming engine 405. When the complex data is used as the parameter, both the phase $\phi_p(n)$ and the amplitude $a_p$ are utilized, thereby allowing estimation of cross correlation with a high degree or precision in the adaptive beamforming engine 405. It is to be noted that T in the formula (7) represents the cycle of the ultrasound wave.

[Formula 5]

$$a_p(n) = \sqrt{\max[C_p(n)]} \quad (5)$$

[Formula 6]

$$\Delta t_p(n) = t_{@max[C_p(n)]} - t_0 \quad (6)$$

[Formula 7]

$$\xi_p(n) = a_p(n)\exp(j\phi_p), \phi_p = 2\pi\frac{\Delta t_p}{T} \quad (7)$$

[Formula 8]

$$I_p = a_p\cos\phi_p(n), Q_p = a_p\sin\phi_p(n) \quad (8)$$

As illustrated in FIG. 2, on the stage subsequent to the extraction converter 413, the adaptive beamforming engine 405 is placed. The adaptive beamforming engine 405 is a block for generating a beamforming output based on the multiple input signals, and serves as a primary operator of the adaptive beamformer (receive beamformer) 107. As illustrated in FIG. 2, the adaptive beamforming engine 405 is provided with a matrix operator 406, an adaptive weight operator 407, and a beamforming operator 408. In the present embodiment, taking an example that the MVDR algorithm is used as the algorithm of the adaptive weight operator 407, the processing of the adaptive beamforming engine 405 will be explained.

In the step 34, the matrix operator 406 calculates the spatial covariance matrix R(n) according to the formula (9). R(n) is computed by using at least one of the following predetermined values; $a_p$, $\Delta t_p(n)$, $\phi_p(n)$, $\xi_p$, and a combination of $I_p$ and $Q_p$, being extracted by the extraction converter 413. Here, an example will be explained as to the case where the complex data $\xi_p$ is used to obtain the spatial covariance matrix R(n) of the formula (9). As expressed by the formula (9), R(n) is obtained by calculating ensemble average of the product between the complex vector $\xi(n)$ expressed by the formula (10), and its complex transpose vector $\xi^H(n)$.

[Formula 9]

$$R(n) = E[\xi(n)\xi^H(n)] \quad (9)$$

$$= E\left\{\begin{pmatrix} \xi_1(n)\xi_1^*(n) & \xi_1(n)\xi_2^*(n) & \cdots & \xi_1(n)\xi_{K-q}^*(n) \\ \xi_2(n)\xi_1^*(n) & \xi_2(n)\xi_2^*(n) & \cdots & \xi_2(n)\xi_{K-q}^*(n) \\ \vdots & \vdots & \ddots & \vdots \\ \xi_{K-q}(n)\xi_1^*(n) & \xi_{K-q}(n)\xi_2^*(n) & \cdots & \xi_{K-q}(n)\xi_{K-q}^*(n) \end{pmatrix}\right\}$$

$$= \frac{1}{N}\sum_{s=-S}^{S}\xi(n-s)\xi^H(n-s)$$

[Formula 10]

$$\xi(n) = [\xi_1(n), \xi_2(n), \ldots, \xi_{K-q}(n)]^T \quad (10)$$

The present invention is characterized in that the similarity being computed by the similarity operator 404 is used as the input (element) in the R(n) of the formula (9). Since the similarity is used, if the size of the received active array 401 is assumed as K, the spatial covariance matrix R(n) becomes a square matrix of (K−q)×(K−q). In a conventional adaptive beamformer, the input into the spatial covariance matrix uses the x(n) in the formula (1), and therefore, the covariance matrix becomes the square matrix of K×K.

It is to be noted that in the formula (9), the ensemble average number N is defined as uniform mean as shown in the rightmost side of the formula (9), assuming N=2S+1 points in total, where there are S samples respectively before and after the target sample point $\xi(n)$.

In the step 35, the adaptive weight operator 407 that has received the spatial covariance matrix R(n) calculates a weight vector w(n) using the MVDR method. The weight vector according to the MVDR method is obtained by the formula (11) in this example here.

[Formula 11]

$$w(n) = \frac{R^{-1}(n)a}{a^H R^{-1}(n)a} \quad (11)$$

In the formula (11), R(n) represents the covariance matrix at a certain sample point n in the time direction, being generated according to the formula (9), and "a" represents a mode vector.

By way of example, if the MVDR method is applied to a received signal sample at a certain one point of time in the linear scan, the complex weight vector w(n) that is obtained assuming the coming direction θ=0° as a direction of interest, serves as an adaptive filter that minimizes a response from any direction other than the direction of interest, and therefore, enhancement of resolution in the orientation direction may be expected. In the present embodiment, since the delay processing is applied in the delay circuit 412 as described above, the input signal is the data with the wave fronts 1000 being aligned in the direction of θ=0°. Therefore, in the formula (9), the mode vector a may be simply assumed as a=[1, 1, . . . , 1]$^T$.

In the step 36, the beamforming operator 408 receives the complex weight vector w(n) obtained by the adaptive weight operator 407, and performs the computations as shown in the formula (12) to the formula (14), together with the received data vector x(n) received from the delay circuit 412 in bypassing manner. Accordingly, the beamforming operator 408 obtains the beamforming output y(n) of one raster that corresponds to the active channel 401.

The formula (12) and the formula (13) indicate the processing of the trapezoidal weighting that degenerates the received data vector x(n) being (K) components upon inputted in bypassing manner from the delay circuit 412, to the vector z(n) made up of (K−q) elements corresponding to the number of the cross correlation functions. In converting the (K) elements to (K−q) elements, any computations may be applicable, as far as it is possible to degenerate from (K) elements to (K−q) elements. Therefore, it is also possible to use any linear operation that is different from the processing of the trapezoidal weighting as indicated by the formula (12) and the formula (13).

[Formula 12]

$$x'_p(n) = [x_p(n), x_{p+1}(n), \ldots, x_{p+K-q-1}(n)]^T \quad (12)$$

-continued

[Formula 13]

$$z(n) = \sum_{p=1}^{q+1} x'_p(n) = [z_1(n), z_2(n), \ldots z_{K-q}(n)]^T \quad (13)$$

[Formula 14]

$$y(n) = w^H(n)z(n) \quad (14)$$

The beamforming output y(n) of one raster obtained by the formula (14) is transferred to the image processor 108, one by one, along with shifting from the active channel 401, to the active channels 402 and 403 on the receive array. In the image processor 108, the scan converter arranges all the rasters and generates a two-dimensional image. In addition, the image processor performs various backend image processing such as various filter processing. Finally, the monitor 103 displays an ultrasound image.

Figure 6:
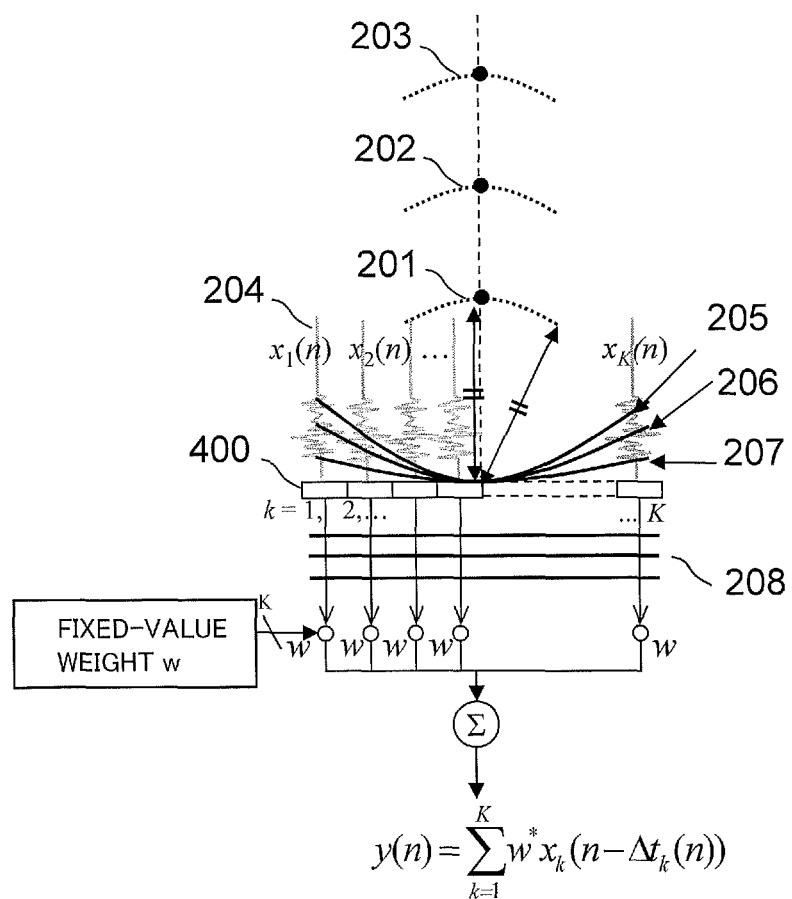
FIG. 6 illustrates the operation of the receive beamformer of the comparative example.

As thus described, in the adaptive method of the present embodiment uses the received signal to obtain the weight vector w(n) by performing the computations, for each sample point in the time direction of the received signal x(n). Then, by subjecting those w(n) and x(n) to computational treatments, thereby obtaining the beamforming output y(n). Accordingly, the weight vector is allowed to be change more adaptively, and therefore, higher-density ultrasound image may be obtained, if it is compared with the case where the weight vector w being the fixed value is used, as illustrated in FIG. 6 as a comparative example.

Further in the present embodiment, the processing for computing the similarity in the time direction is performed in advance, and the adaptive beamforming engine 405 is allowed to correct the fluctuations in the time direction with relatively a small amount of computations, thereby enabling more accurate estimation of the point image. Accordingly, it is possible to correct image blurring in the time direction (depth direction), and obtain a sharper point image. In addition, an ultrasound image including little false images and noise may be obtained stably.

Figure 5:
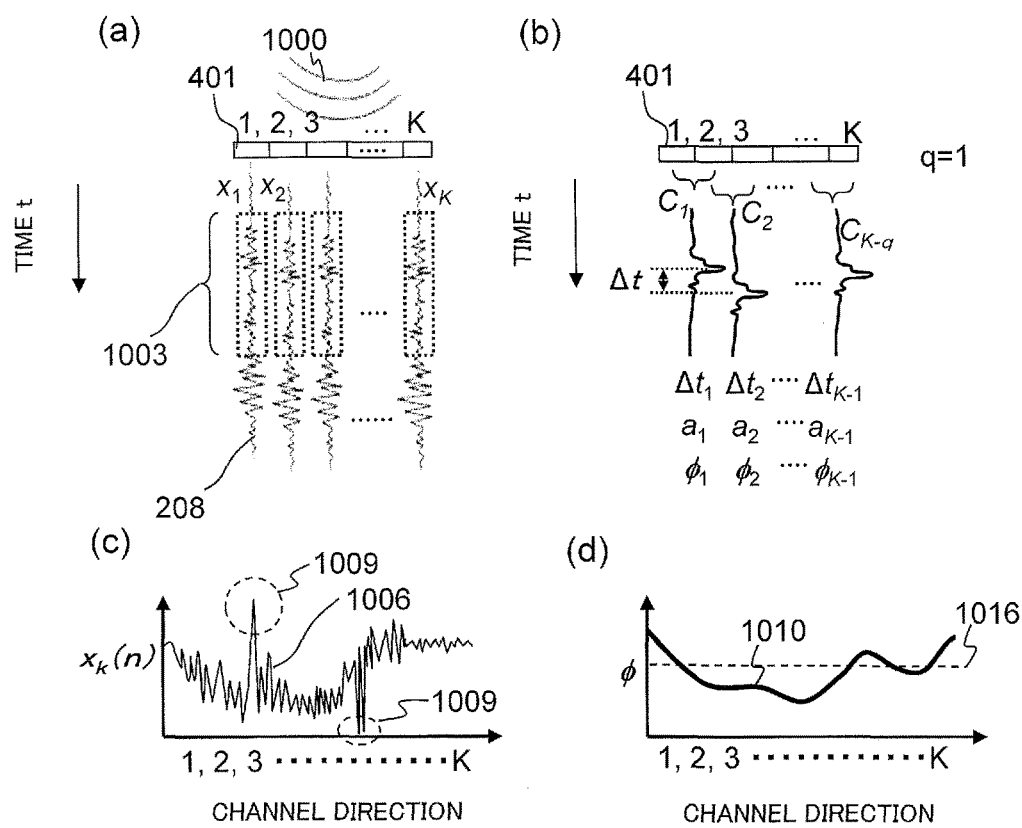
FIG. 5(a) illustrates the received signals 208 in which the wave fronts are aligned by the processing of the delay circuit 412 according to the first embodiment.
FIG. 5(b) illustrates the similarity function obtained by the similarity operator 404 and an example of the index value extracted by the extraction converter 413.
FIG. 5(c) is a graph showing the distribution of the output in the channel direction at the sample time n, as to the received signals with the wave fronts being aligned.
FIG. 5(d) is a graph showing a distribution of the index ($\phi$) in the channel direction at the sample time n of the similarity function.

With reference to FIG. 5(*c*) and FIG. 5(*d*), an explanation will be provided as to an effect produced by performing the processing for computing the similarity. FIG. 5(*c*) illustrates plotting at a certain sample point of time n, with the output x(n) from the delay circuit 412 as the vertical axis, and with the channel number as the horizontal axis. FIG. 5(*d*) illustrates plotting at a certain sample point of time n, with the value extracted by the extraction converter 413 as the vertical axis, indicating the characteristics of the output of the computation result $C_p$ from the similarity operator 404 (any of the parameters; $a_p$, $\Delta t_p(n)$, $\phi_p(n)$, $\xi_p(n)$, and a combination of complex components $I_p$ and $Q_p$, and $\phi_p(n)$ is extracted in this example here), and with the channel number as the horizontal axis.

As illustrated in FIG. 5(*c*), a profile of the received signals in the channel direction indicate the RF signals (received signals) of a sound wave, being placed side by side without any change, and thus it includes much noise, and in some cases, a jump 1009 may occur in the profile, due to influence of micro scattering substances and noise. Though it is possible to mitigate the influence of the jump 1009 by taking an average in the time direction, there is a limit thereto. Therefore, if the RF signals as shown in FIG. 5(*a*) without any change, or an arithmetic average thereof taken in the time direction, and thereafter inputted in the adaptive beamforming engine, the weight w(n) being obtained may be influenced by the noise and/or the jump 1009. In particular, in the case where the adaptive beamformer such as the MVDR method is applied to the RF signals, the weight w(n) is generated in a manner as focusing on the jump 1009 of data. Therefore, a false image may be generated at the position of the jump 1009, for the case where no objects exists actually. By way of example, if the similarity computation is not performed (i.e., the estimation in the time direction is not performed), there is no other way but assuming the fixed phase 1016 as the phase ϕ that is used for the estimation by the adaptive beamforming engine, the fixed phase 1016 being almost out of phase with the actual phase 1010 as shown in FIG. 5(*d*). Therefore, the estimation precision in the time direction may be decreased, and an image quality of a final ultrasound image may be deteriorated.

On the other hand, in the present embodiment, in the similarity computation performed by the similarity operator 404, matched filter processing in the formula (2) is performed, assuming a wave as one packet. Therefore, as shown in FIG. 5(*b*), an averaging action in the time direction is obtained, thereby acquiring the channel-direction profile 1010 in which the noise is reduced. By way of example, the phase 1010 extracted by the extraction converter 413 from the computation result of the similarity operator 404 is used, thereby allowing estimation with a higher degree of precision in the time direction, and producing an effect that the point image of the final ultrasound image is rendered to be a sharp image with a spot small in diameter in the time direction (ultrasound wave propagating direction).

It is also possible to perform a spatial average operation using a subarray matrix, as one of the other methods of computational algorithm in the matrix operator 406 as described above. The subarray matrix is expressed by the formula (15) and the formula (16).

[Formula 15]

$$R_{\tilde{l}}(n) = \tilde{\xi}_{\tilde{l}}(n)\tilde{\xi}_{\tilde{l}}^H(n) \quad (15)$$

[Formula 16]

$$\tilde{\xi}_{\tilde{l}}(n) = [\xi_l(n), \xi_{l+1}(n), \ldots, \xi_{l+L-1}(n)]^T \quad (16)$$

A main diagonal component of the subarray matrix is made to shift one sample by one sample, in accordance with the main diagonal component of the covariance matrix R(n), so as to perform the spatial average operation of ((K−q)−L+1) subarray matrixes, and the covariance matrix R^(n) in the formula (17) is obtained. When this covariance matrix R^(n) is subjected to the computation in the adaptive weight operator 407, the covariance matrix R^(n) is substituted for R(n) in the aforementioned formula (11), and the weight w^(n) is calculated. The beamforming operator 408 uses the formula (18) and the formula (19) to output the beamforming output y(n).

[Formula 17]

$$R^{\wedge}(n) = \frac{1}{N(K-q-L+1)} \sum_{s=-S}^{S} \sum_{l=1}^{K-q-L+1} R_{\tilde{l}}(n-s) \quad (17)$$

[Formula 18]

$$\tilde{z}_l(n) = [z_l(n), z_{l+1}(n), \ldots, z_{l+L-1}(n)]^T \quad (18)$$

[Formula 19]

$$y(n) = w^{\wedge H}(n) \sum_{l=1}^{K-q-L+1} \tilde{z}_l(n) \quad (19)$$

As described above, the spatial average operation of the subarray matrix is performed in the matrix operator 406, thereby producing an effect that the noise caused by correlation in the received ultrasound signals is restrained. In addition, as one of the spatial averaging methods, it is also possible to perform a publicly known forward/backward spatial average processing.

In the present embodiment as described above, an explanation has been provided as to an example for obtaining the similarity between one received signal and another signal "q" channels away, in the similarity operator 404. For example, in the case where the similarity of the received signals is obtained between the adjacent channels where q=1, the similarity operator 404 outputs (K−1) cross correlation functions, and thus, the number of the vector elements in the formula (10) and the formula (11) computed in the adaptive beamforming engine 405 also becomes (K−1). Therefore, prior to subjecting the received data vector x(n) and the complex weight vector w(n) to the computation process, it is necessary, according to the formula (12) and the formula (13), to make the received data vector x(n) to degenerate into the vector z(n), which is made up of (K−1) elements, corresponding to the number of the cross correlation functions. In order to avoid the computations in the formula (12) and the formula (13), the similarity operator 404 obtains a self-correlation function of the input data $x_K(n)$ in the K-th channel, as shown in the formula (20), and the result $C_K(n)$ may be used as the K-th cross correlation function when the similarity q=1.

Accordingly, as shown in the formula (21) and formula (22), it becomes possible to prepare the vectors as shown in the formula (10) and the formula subsequent thereto while maintaining the channel number K, and this allows the received signal x(n) being inputted in bypassing manner to be used without degeneration. Ultimately, the beamforming output may be obtained according to the formula (23).

[Formula 20]

$$C_K(n)=\int_{-r}^{r} x_K(n)x_K(n+\tau)d\tau \quad (20)$$

[Formula 21]

$$\xi(n)=[\xi_1(n),\xi_2(n),\ldots,\xi_K(n)]^T \quad (21)$$

[Formula 22]

$$z(n)=x(n)=[x_1(n),x_2(n),\ldots,x_K(n)]^T \quad (22)$$

[Formula 23]

$$y(n)=w^H(n)x(n) \quad (23)$$

As discussed above, the present embodiment is characterized in that the similarity computation is performed on the received signals from the multiple elements in the receive array, as an algorithm of the adaptive beam forming, and by using the result of the computation, the spatial covariance matrix R(n) is generated. Therefore, the adaptive weight operator 407 may employ any algorithm for performing the beamforming based on the spatial covariance matrix R(n). In other words, it is possible to use not only the MVDR method, but also the MUSIC (Multiple Signal Classification) method, the APES (Amplitude and Phase Estimation) method, the method of ESPRIT (Estimation of Signal Parameters via Rotational Invariance Techniques), the MEM (Maximum Entropy Method), or the like, for instance.

Second Embodiment

Figure 7:
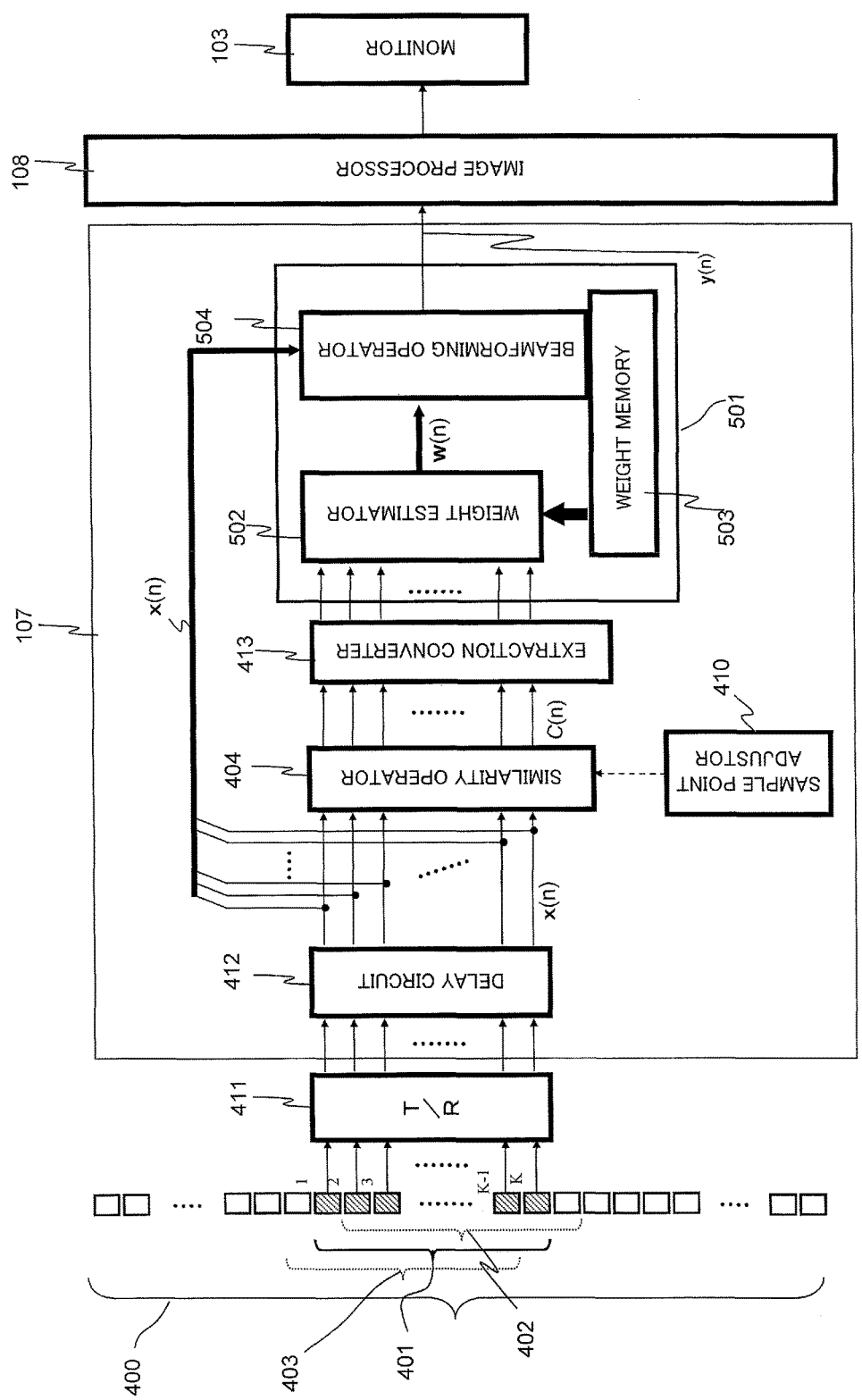
FIG. 7 is a block diagram illustrating a configuration of the receive beamformer according to the second embodiment.
Figure 8:
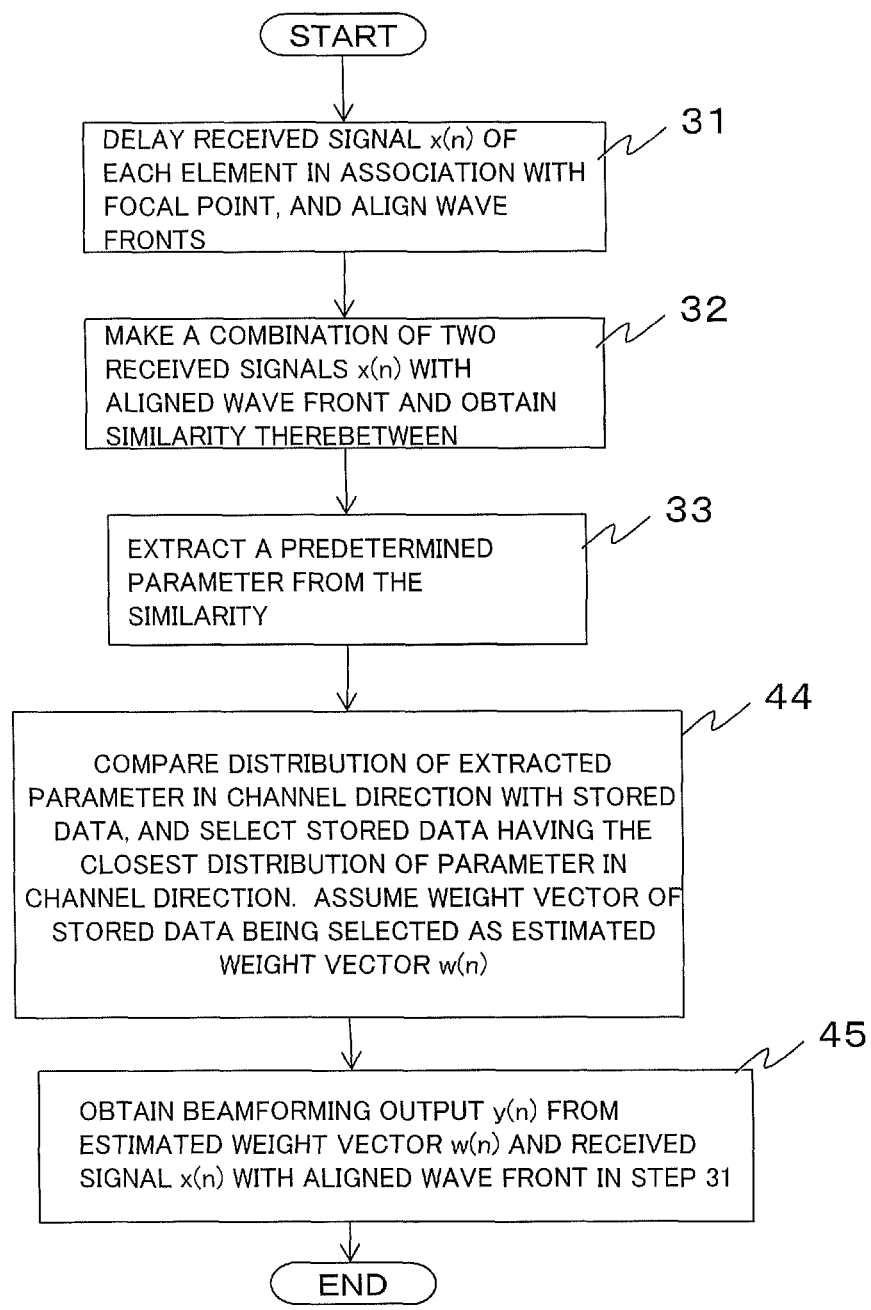
FIG. 8 is a flowchart showing the signal processing in the receive beamformer according to the second embodiment.

With reference to FIG. 7, the ultrasound imaging apparatus according to the second embodiment of the present invention will be explained. FIG. 7 is a block diagram showing the receive beamformer 107 according the second embodiment. FIG. 8 is a flowchart illustrating the operations of each component in the receive beamformer 107.

In the second embodiment, the adaptive weight operator incorporates a weight memory for storing in advance multiple-type combinations of a distribution of the similarity and the weight value, and a weight estimator. The weight estimator selects a combination of the distribution of the similarity and the weight value being stored in the weight memory, based on multiple distributions of the similarity received from the similarity operator, thereby enabling a selection from the weight values associated with the multiple distributions of the similarity received from the similarity operator.

Specifically, as illustrated in FIG. 7, the receive beamformer 107 of the second embodiment is different from the receive beamformer 107 of the first embodiment in FIG. 2, in the configuration of the adaptive beamforming engine 501. The configuration except the receive beamformer is the same as the first embodiment, tedious explanations will not be provided.

In the second embodiment, as shown in FIG. 7, the adaptive beamforming engine 501 is provided with a weight estimator 502, a weight memory 503, and the beamforming operator 504. The adaptive beamforming engine 405 of the first embodiment in FIG. 2 performs the similarity computation and the adaptive weight computation, for one sample each (or every some samples) in the time direction of the receive data x(n), and the adaptive beamforming is performed sequentially. The second embodiment is characterized in that the weight computation is not performed for each sample. In the second embodiment, the weight memory 503 (Look Up Table: LUT) stores in advance, similarity extraction values being preliminarily assumed and weight vectors w(n) respectively associated with the assumed similarity extraction values. The weight estimator 502 estimates a weight based on the weight vectors w(n) in the weight memory 503.

Specifically, the weight memory 503 stores, according to a preliminary off-line processing, a distribution in the channel direction (e.g., n=1 to (K−q)) of the values (e.g., $\phi_p(n)$) assumed in advance, of the predetermined parameter indicating the similarity of the received signal x(n) (at least one predetermined parameter from the following; $a_p$, $\Delta t_p(n)$, $\phi_p(n)$, $\xi_p(n)$, and a combination of complex components $I_p$ and $Q_p$). In addition, the weight memory 503 stores for each distribution of the aforementioned parameter, the weight vector w(n) obtained according to the computation in advance, in association with the distribution of the parameter value. The weight vector w(n) is computed by the algorithm according to the matrix operator 406 and the adaptive weight operator 407 in the adaptive beamformer of the first embodiment.

The operations of the receive beamformer 107 according to the present embodiment will be explained. In the steps 31 to 33 in FIG. 8, in the same manner as the steps 31 to 33 of the first embodiment in FIG. 3, in the transmit-receive separation circuit 411, the delay circuit 412, the similarity operator 404, and the extraction converter 413, similarity is computed as to the received signal x(n) with the wave fronts being aligned by the delay process, and the predetermined parameter (e.g., $\phi_p(n)$, n=1 to (k−q)) is extracted based on the similarity. This parameter is identical to the parameter whose distribution in the channel direction is stored in the weight memory 503.

In the step 44, the weight estimator 502 compares the distribution in the channel direction, as to the predetermined parameter indicating the similarity, received from the extraction converter 413, with the data stored in the weight memory 503, and selects the stored data having the distribution being the closest to the distribution of the parameter in the channel direction. In order to select the stored data being the closest to the distribution of the parameter in the channel direction, it is possible to use an existing curb fitting algorithm, such as the maximum likelihood estimation, least squares method, and recursive fitting algorithm by polynomial approximation. The weight estimator 502 transfers to the beamforming operator 504, the weight vector w(n) stored in association with the stored data indicating the selected distribution of the parameter in the channel distribution, as the estimated weight vector.

In the step 45, the beamforming operator 504 performs computations, as to the estimated weight vector w(n) and the received signal x(n) received from the delay circuit 412 in a bypassing manner, through the use of any of the formula (14), the formula (19), and the formula (23), and obtains the beamforming output y(n) of one raster in association with the active channel 401.

In the configuration of the second embodiment, using the adaptive beamforming engine 501 in FIG. 7 avoids one-by-one calculation of the weight. Therefore, it is possible to reduce the computation cost drastically, relative to the case where the adaptive beamforming engine 405 in FIG. 2 is used.

The present embodiment is directed to a configuration where signals obtained by subjecting the received signals to the similarity computation are inputted into the adaptive beamforming engine 501. In the first embodiment, as explained with reference to FIG. 5(d), the signals subjected to the similarity computation in advance have little noise in the profile in the channel direction, achieving high signal stability. Therefore, in the second embodiment, even in the case where LUT-type adaptive beamforming engine 501 is used as the adaptive beamforming engine, it is possible to perform weight estimation with a high degree of precision. By way of example, if the LUT-type adaptive beamforming engine 501 is employed using the channel distribution 1006 including much noise and jumps as illustrated in FIG. 5(b), the degree of precision in the weight estimation may become low. On the other hand, as in the present embodiment, if a distribution is used which has been subjected to the cross correlation processing in the similarity operator 404, this enables more accurate approximation in the weight estimator 502, for instance, enabling polynomial approximation to be performed, and therefore, it is possible to enhance the degree of precision of the channel weighting estimation, through the use of the weight memory 503.

Third Embodiment

The third embodiment is directed to a configuration where the adaptive weight operator has both the first operator and the second operator. The first operator uses the similarity obtained by the similarity operator to perform the adaptive signal processing, and computes the adaptive weight. The second operator is provided with the weight memory that stores in advance, multiple-type combinations of the distribution of similarity and the weight value, and the weight estimator. The weight estimator selects a combination of the distribution of the similarity and the weight value, being stored in the weight memory, thereby allowing a selection from the weight values associated with multiple distributions of the similarity received from the similarity operator. In addition, the adaptive weight operator may be provided with at least one of a drive switching part and an output switching part; the drive switching part is provided for selectively driving the first operator or the second operator, and the output switching part is provided for selectively transferring to the image processor, an output from either of the first operator and the second operator.

Figure 9:
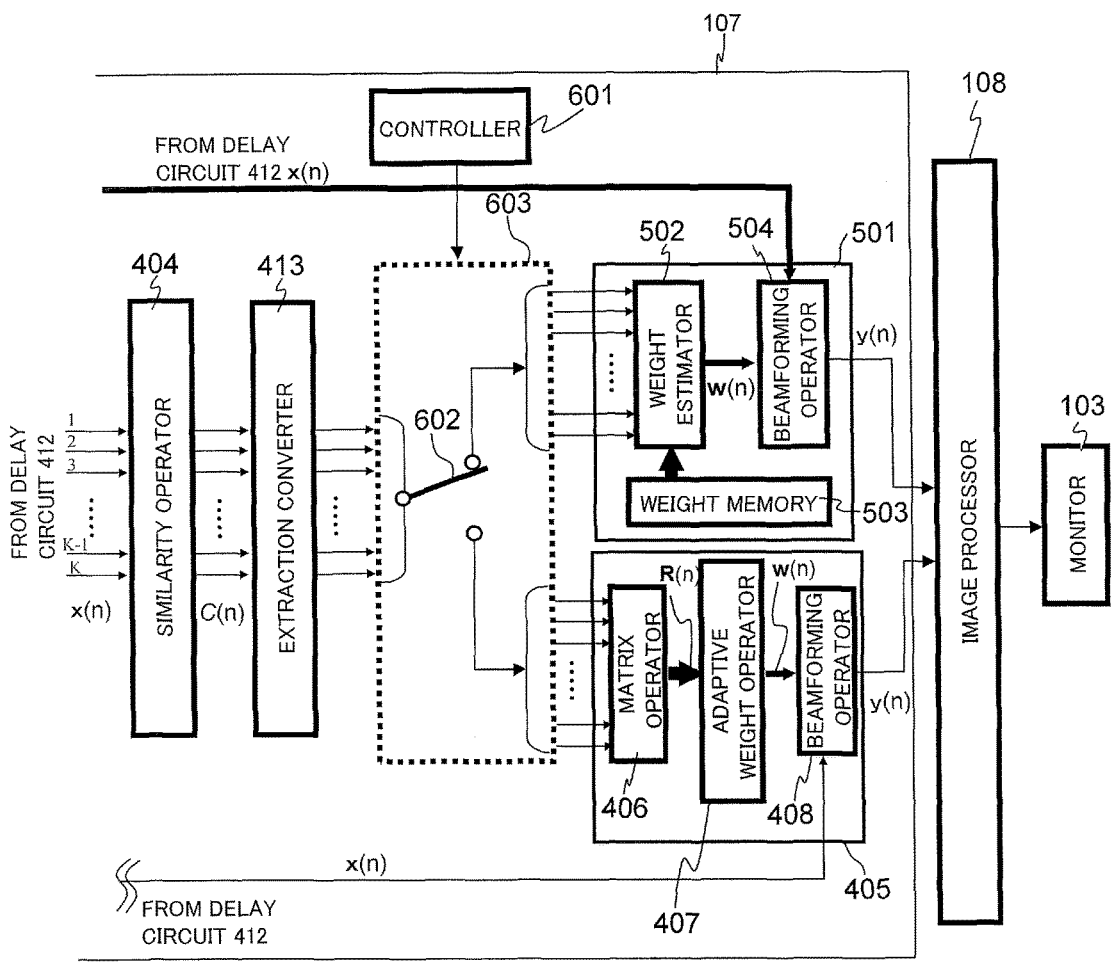
FIG. 9 is a block diagram illustrating a configuration of the receive beamformer according to the third embodiment.

Hereinafter, with reference to FIG. 9, the ultrasound imaging apparatus according to the third embodiment of the present invention will be explained specifically. FIG. 9 is a block diagram illustrating a part of the receive beamformer according to the third embodiment. The receive beamformer of the third embodiment includes a dual beamforming engine as illustrated in FIG. 9, being provided with, as the adaptive beamforming engine, both the adaptive beamforming engine 405 of the first embodiment and the beamforming engine 501 of the second embodiment. The adaptive beamforming engine 405 of the first embodiment is referred to as a sequential-type adaptive beamforming engine, and the adaptive beamforming engine 501 of the second embodiment is referred to as the LUT-type adaptive beamforming engine.

In the third embodiment, there are provided a switching part 603 for selectively activating either one of the two types beamforming engines 501 and 405, and a controller 601 for controlling the switching part 603. The switching part 603 is provided with a switch 602 for transferring the output from the extraction converter 413 to either of the two-types beamforming engines 501 and 405.

The configuration and operations of each of the beamforming engines 501 and 405 are the same as those explained in the first and the second embodiments, and therefore, they will not be explained tediously.

In the configuration of the third embodiment, the operator of the ultrasound imaging apparatus determines as to switching of the beamforming engines, based on the magnitude of the contrast ratio of the ultrasound image of the test subject, and the magnitude of temporal/spatial fluctuations of the ultrasound image, allowing the operator to instruct the controller 601 which of the two-type beamforming engines is to be used; the beamforming engine 501 or the beamforming engine 405. According to this configuration, it is possible to provide an ultrasound image, by selectively using the beamforming engine suitable for the condition of the test subject.

Fourth Embodiment

The fourth embodiment is directed to a configuration that a subtraction part obtains a difference between a computation result of the first operator and a computation result of the second operator in the third embodiment, and according to the difference obtained by the subtraction part, the weight changer changes the weight value stored in the weight memory of the second operator.

Figure 10:
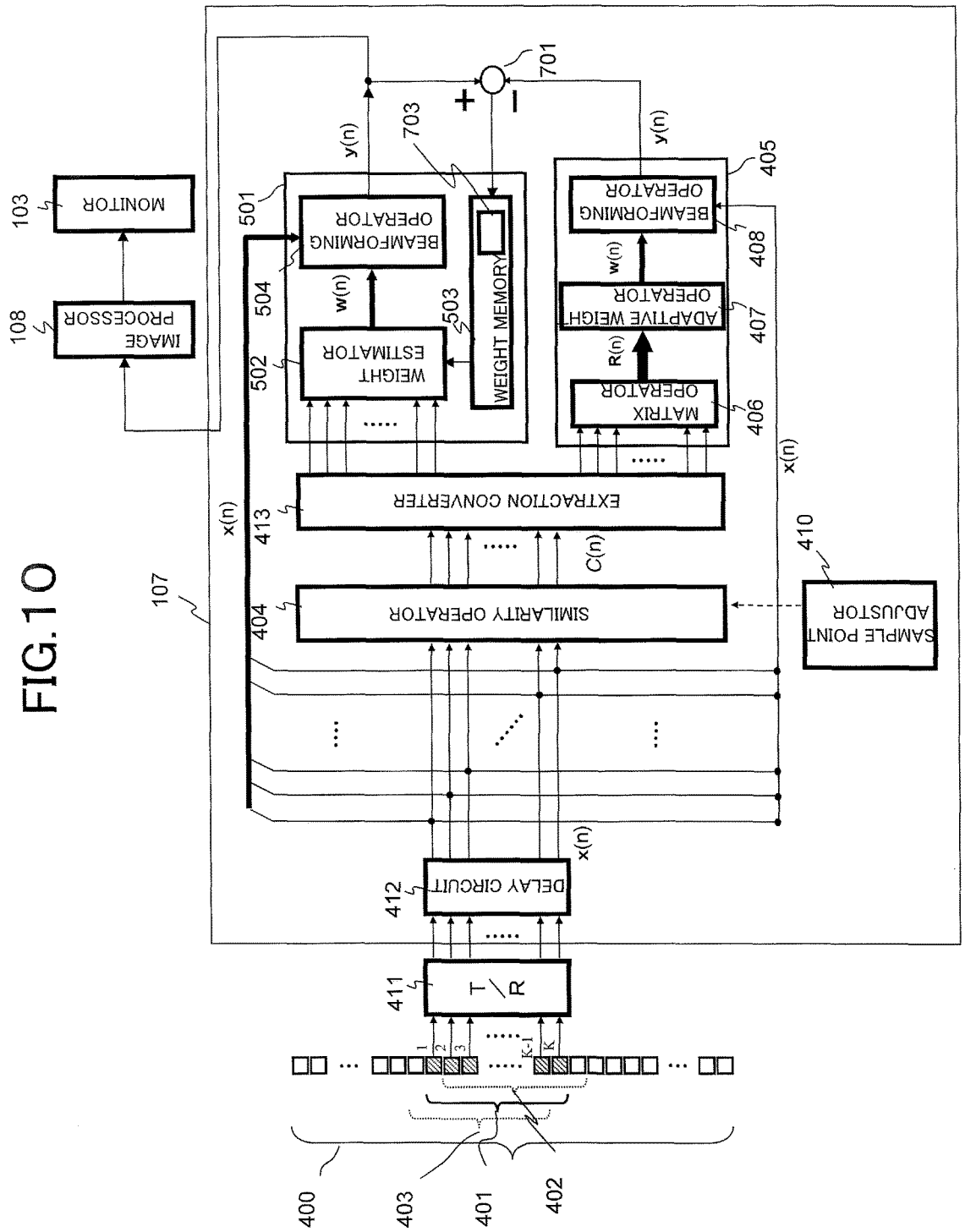
FIG. 10 is a block diagram illustrating a configuration of the receive beamformer according to the fourth embodiment.

With reference to FIG. 10, the ultrasound imaging apparatus according to the fourth embodiment of the present invention will be explained. FIG. 10 is a block diagram illustrating the receive beamformer 107 according to the fourth embodiment.

In the receive beamformer 107 of the fourth embodiment as shown in FIG. 10, a feedback group is added to the dual beamforming engine 501 and 405 of FIG. 9 according to the third embodiment. Specifically, there is provided a subtraction part 701 for calculating a difference between the beamforming output y(n) from the LUT-type beamforming engine

501 and the beamforming output y(n) from the sequential-type beamforming engine 405. A difference output from the subtraction part 701 is inputted into the weight memory 503. The weight changer 703 is placed in the weight memory 503, and the weight changer changes the value of the weight w(n) stored in advance in the weight memory 503, based on a difference output from the subtraction part 701. Specifically, the weight changer 703 performs computations according to a predetermined algorithm, thereby assuming the difference output from the output part 701 as an error, and changing the value of the weight w(n) being stored in advance in the weight memory 503 so that the error becomes minimum.

Any algorithm is applicable to the computation in the weight changer 703, as far as the algorithm is able to minimize the error. It is preferable, however, to utilize the algorithm that is similar to the MMSE (Minimum Mean Square Error), for instance. As the algorithm of the MMSE, it is possible to use any one of the following; LMS (Least-Mean Squares) based on a steepest descent method, SMI (Sample Matrix Inversion) being a direct solution method of a sample value, and RLS (Recursive Least Square: recursive least squares method) like the Kalman filter.

As discussed above, in the fourth embodiment, it is possible to perform calibration for making the weight value w(n) obtained by the weight estimation by the LUT-type adaptive beamforming engine 501 to be close to the weight value w(n) that is computed in the sequential-type adaptive beamforming engine 405. Therefore, upon starting the imaging, both the LUT-type adaptive beamforming engine 501 and the sequential-type adaptive beamforming engine 405 are activated, and the subtraction part 710 performs the feedback operation, thereby optimizing the weight value within the weight memory 503 in the LUT-type adaptive beamforming engine 501. Once the optimization is completed, the sequential-type adaptive beamforming engine 405 and the subtraction part 701 are stopped, and according to the weight estimation performed only by the LUT-type adaptive beamforming engine 501, it is possible for the LUT-type adaptive beamforming engine 501 to estimate the weight w(n) similar to that of the sequential-type adaptive beamforming engine 405, and perform the beamforming computation.

Accordingly, compared to the second embodiment, though the calculation burden is increased a little, the weight value in the weight memory 503 of the LUT-type adaptive beamforming engine 501 is able to be changed to an optimum weight value w(n), and thus, it is possible to provide an ultrasound image that is more suitable for the condition of the test subject.

In the present embodiment, the adaptive beamforming engines 405 and 501 receive inputs of signals being obtained by subjecting the received signals to the similarity computation, and including little noise and being high in stability. With this configuration, even in the case where the LUT-type adaptive beamforming engine 501 is employed as discussed in the second embodiment, the degree of precision of the channel weighting estimation is high. Therefore, in the present embodiment, in the configuration of the dual adaptive beamforming engine utilizing the feedback loop, perturbation is decreased in the output from the subtraction part, being assumed as an error amount, thereby achieving a stable feedback processing. In addition, in the weight changer 703, upon performing the computation for changing the weight value to a value that makes the error minimum, according to the MMSE, or the like, the number of iterative computations may be reduced, and the computation cost may also be reduced.

Fifth Embodiment

Figure 11:
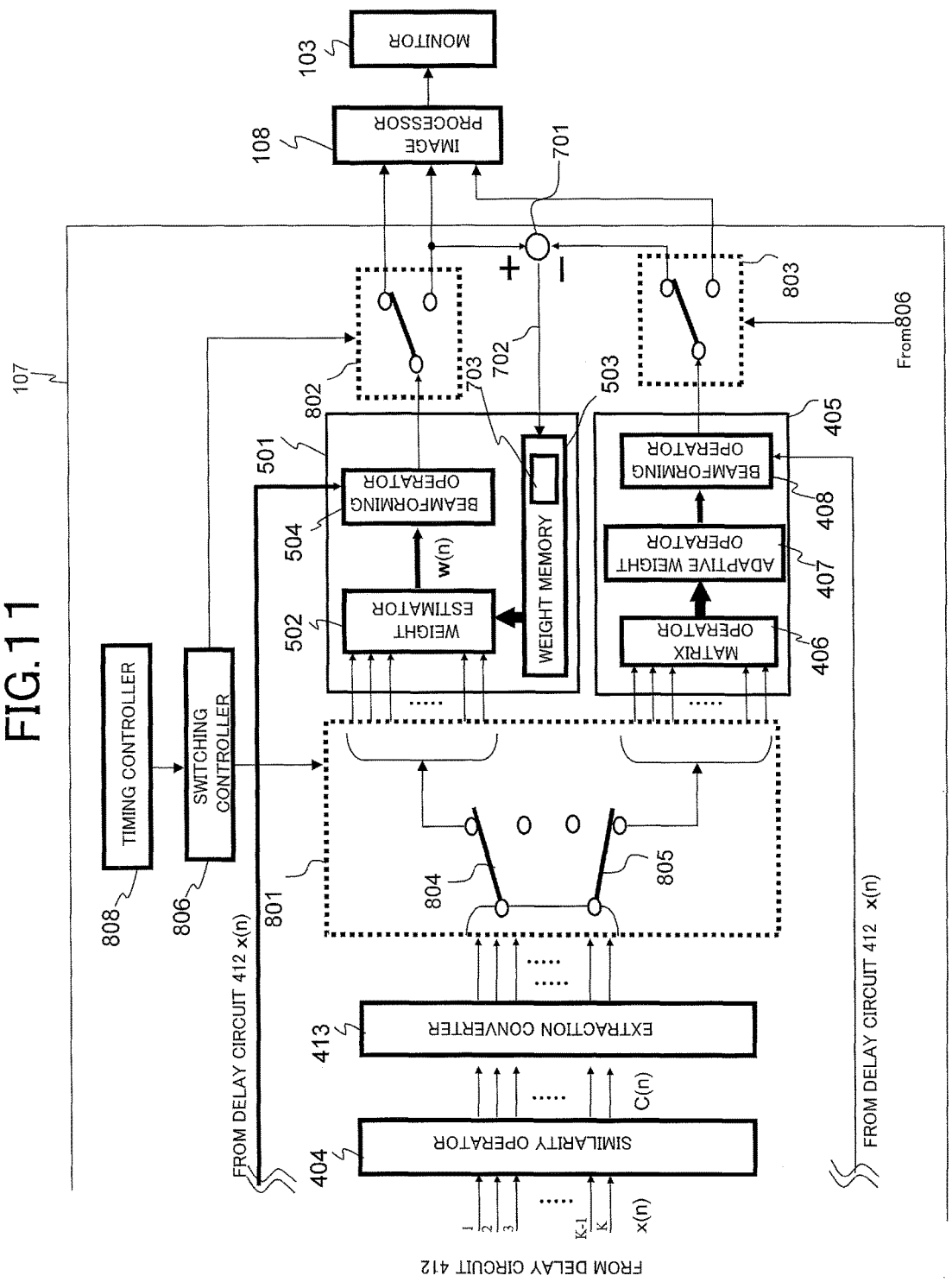
FIG. 11 is a block diagram illustrating a configuration of the receive beamformer according to the fifth embodiment.

With reference to FIG. 11, the ultrasound imaging apparatus according to the fifth embodiment of the present invention will be explained. FIG. 11 is a block diagram illustrating the receive beamformer 107 according to the fifth embodiment.

The receive beamformer 107 in FIG. 11 has a configuration that in addition to the dual beamforming engine 501 and 405 with the feedback loop by the subtraction part 701, similar to the fourth embodiment, switching parts 801, 802, and 803 for switching the beamforming engines are provided. There are arranged the switching controller 806 for controlling the switching operations of the switching parts 801, 802, and 803, and a timing controller 808 for providing an instruction with regard to the switching timing, to the switching controller 806.

In the configuration of FIG. 11, in response to the control signal from the switching controller 806, the switches 804 and 805 in the switching part 801, the switching parts 802 and 803 are switched, thereby selectively transfer any of the following to the image processor 108; a beamforming output from the sequential-type beamforming engine 405, a beamforming output from the LUT-type beamforming engine 501, or a beamforming output from the LUT-type beamforming engine 501 via the feedback loop according to the subtraction part 701.

Further in the configuration of FIG. 11, the timing controller 808 is able to control the switching timing of the switching controller 806. Accordingly, by way of example, if the movement of the test subject (patient) during the operation is large, or the like, the feedback loop according to the subtraction part 701 is iterated, increasing the number of updating the weight value in the weight memory 503, so as to follow the movement. On the other hand, if the movement of the test subject is small, the feedback loop according to the subtraction part 701 is not iterated, and the computing burden is reduced, thereby flexibly managing the computation scheme of the adaptive ultrasound image and various applications thereof, such as assigning a part of the calculation cost to other image processing algorithms in the image processor 108.

Sixth Embodiment

With reference to FIG. 12(*a*) and FIG. 12(*b*), the sixth embodiment of the present invention will be explained. FIG. 12(*a*) is a block diagram illustrating the similarity operator 404, and the extraction converter 413 of the present embodiment. FIG. 12(*b*) illustrates a processing of the decimating operator of FIG. 12(*a*).

As illustrated in FIG. 12(*a*), in the present embodiment, there is provided a switching part 902 within the similarity operator 404. The switching part 902 performs switching whether the signals inputted from the delay circuit 403 into the similarity operator 404 are subjected to the similarity computation process as performed in the first embodiment, and the like, or the signals are transferred to the extraction converter 413 as they are, without performing the similarity computation.

The extraction converter 413 is provided with the extraction operator 905 for performing computations for extracting a predetermined parameter, similar to the first embodiment and the like, and the decimating operator 904. Within the extraction operator 905, a switching part (parameter (index) switching part) 903 for switching the types of parameters to be extracted from the computation result $C_p(n)$ of the similarity operator. The decimating operator 904 decimates the output from the extraction operator 903, and outputs the result to the beamforming engines 405 and 501.

An extraction parameter changer 901 is connected to the switching parts 902 and 903, so as to control the operations of those switching parts.

The extraction parameter changer 901 switches the switching part 902 according to an instruction from a manipulator (operator), thereby allowing a selection whether the signals inputted to the similarity operator 404 from the delay circuit 403 are transferred as they are, to the extraction operator 905, or a result after applying the similarity computation is transferred to the extraction operator 905. Further by switching the switching part 903, it is possible to change which parameter is extracted by the extraction operator 905, based on the signals received from the similarity operator 404. In other words, it is possible to select from one of the following, and switched thereto; the peak amplitude $a_p(n)$, peak time lag $\Delta t_p(n)$, phase $\phi$, or complex signals ($\xi_p(n)$, $I_p(n)$, $Q_p(n)$).

The decimating operator 904 decimates in the time direction, a result of the similarity computation or the output from the delay circuit 403, received from the extraction operator 905, and outputs the result of decimation. Specifically, as shown in FIG. 12(*b*), the decimating operator 904 decimates the output from the extraction operator 905 at a predetermined interval, and outputs the result. In other words, during the period 1014 from the sample point of time n to the sample point of time n+4, an average of the output at the sample point of time n and the output at the sample point of time n+5 is continued to be outputted from the extraction operator 905. During the period 1015 from the sample point of time n+5 to the sample point of time n+9, an average of the output at the sample point of time n+5 and the output at the sample point of time n+9 is continued to be outputted. As described above, during a predetermined period of the sample points of time (e.g., 5 samples) 1014 and 1015, the same value is continued to be outputted, thereby reducing the burden on the computation in the beamforming engines 405 and 501 in the subsequent stage. Byway of example, if the outputs are decimated every five samples, the processing cost for the beamforming engine may be reduced to one-fifth of the cost. In addition, since the average taken with the output in the subsequent period is employed as the output during the predetermined periods 1014 and 1015, it is possible to prevent significant fluctuation of the output, which may be caused by decimating the samples.

In the sixth embodiment, as the configuration other than above, any of the configurations in the first to the fifth embodiment may be employed.

(Console of Ultrasound Diagnostic Apparatus)

Figure 13:
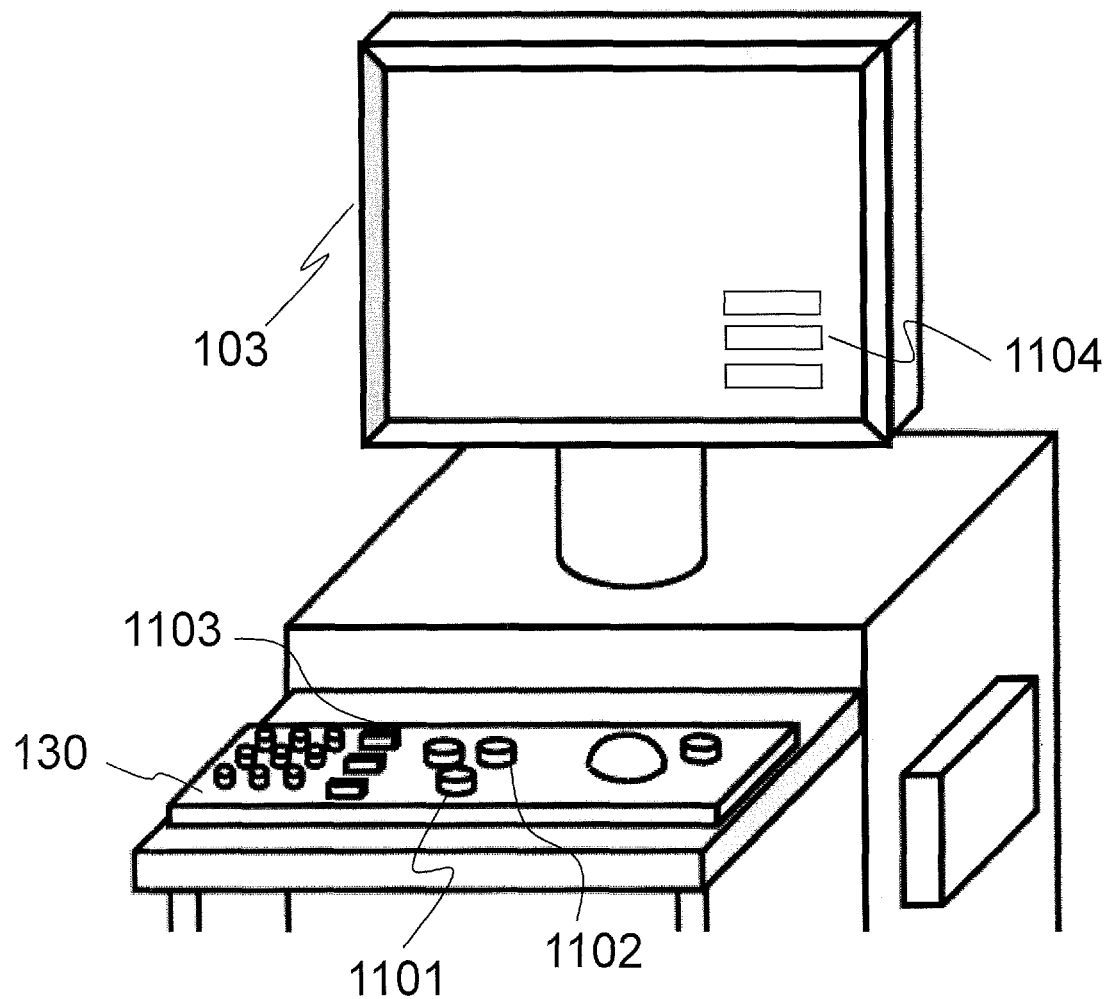
FIG. 13 is a perspective view of a console of the ultrasound imaging apparatus according to the present embodiments.

FIG. 13 illustrates a console 130 of the ultrasound imaging apparatus of the present invention. As illustrated in FIG. 13, some of the characteristics of the embodiments as described above may be arranged in the console of the ultrasound diagnostic apparatus. By way of example, the controller 601 in FIG. 9 and the switching controller 806 in FIG. 11, for selectively activating two types of beamforming engines 405 and 501, and the extraction parameter changer 901 in FIG. 12, are arranged in the form of switch part 1103 of the console as shown in FIG. 13. This configuration allows the operator to switch the types of the beamforming engines, and the types of extraction parameters. The switching timing controller 808 in FIG. 11, and the sample point adjuster 410 in FIG. 2, FIG. 7, FIG. 10, an FIG. 12 may be arranged on the console, in the form of tabs 1101 and 1102 with marks, and the like. With this configuration, it is possible for the operator to change explicitly, a value of repeat timing that indicates, for example, how many times the LUT-type beamforming engine 501 is activated before activating the sequential-type beamforming engine 405 once, and to change the number of correlation sample points (r in the formula (2)). This configuration allows the operator to change various parameters of the adaptive beamformer, while checking the actual ultrasound image, thereby undertaking diagnostic evaluation in an optimum condition that depends on the patient. It is also possible to configure such that the set values are displayed in a part 1104 of the display area on the monitor 103.

(Examples of Effects Produced by the Aforementioned Embodiments)

Figure 14:
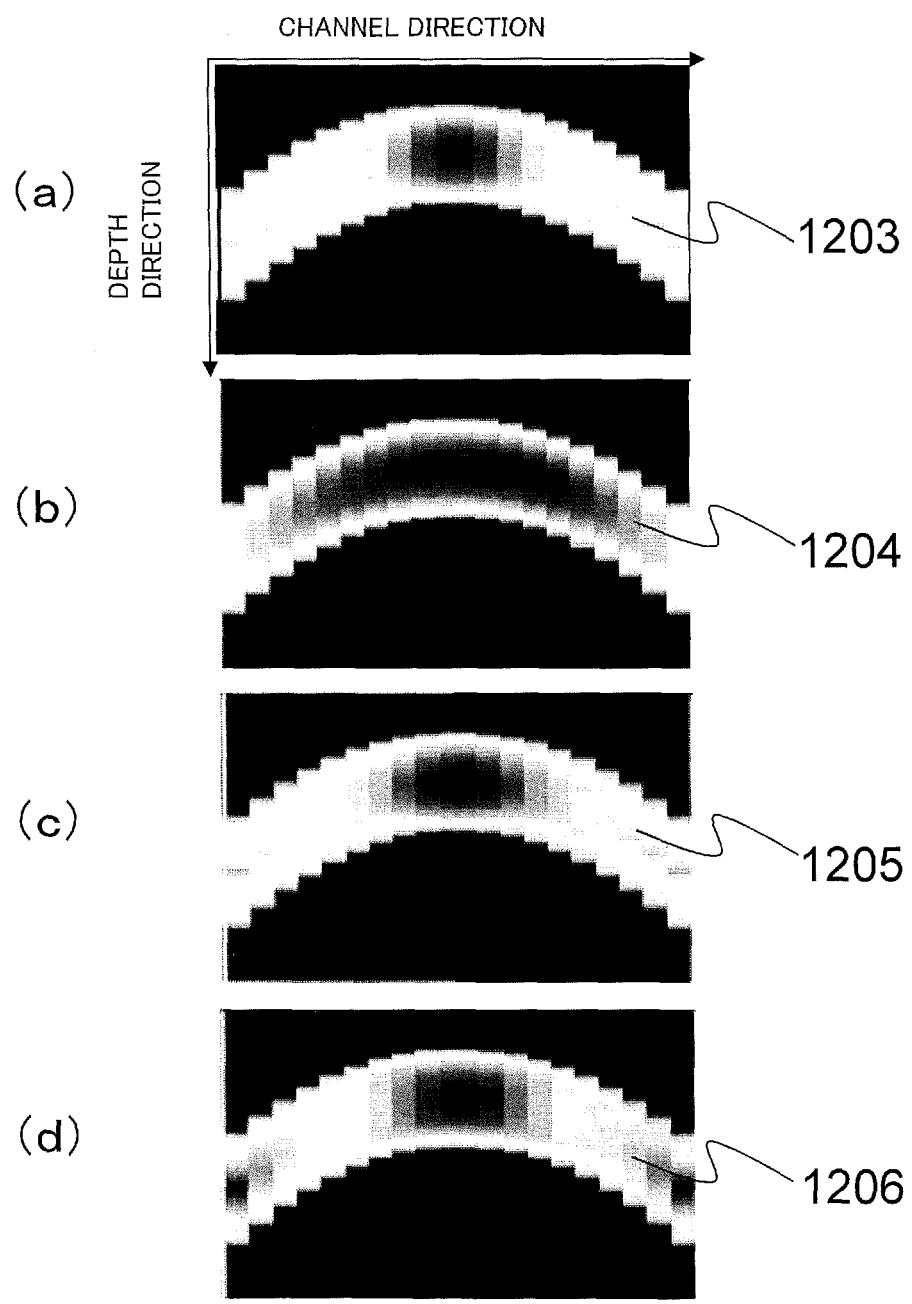
FIG. 14(a) illustrates an image obtained by the ultrasound imaging apparatus according to the first embodiment.
FIG. 14(b) illustrates an image of the comparative example, obtained by a conventional delay-and-sum method (without the similarity computation nor the adaptive beamforming engine 405)
FIG. 14(c) illustrates an image of the comparative example, obtained by the averaging process in the time direction using only the adaptive beamforming engine.
FIG. 14(d) illustrates an image of the comparative example, obtained using only the adaptive beamforming engine without performing the averaging in the time direction.

With reference to FIG. 14(*a*) to FIG. 14(*d*), effects of the aforementioned embodiments will be explained. In FIG. 14(*a*) to FIG. 14(*d*), the receive beamformer, and the like, of the present embodiment and the comparative example are used to generate an ultrasound image from echo signals being point scatterers. In all the images from FIG. 14(*a*) to FIG. 14(*d*), the channel direction (aperture direction) of the array-like elements (ultrasound transducer) 400 is assumed as a horizontal axis, and the ultrasound propagating direction is assumed as the vertical axis, being the direction downwardly away from the elements 400.

The ultrasound image 1203 in FIG. 14(*a*) is obtained by the first embodiment that uses the similarity operator 404 and the adaptive beamforming engine 405, and the ultrasound image 1204 in FIG. 14 (*b*) is obtained as a comparative example, by a conventional-type delay-and-sum method (without the similarity computation nor the adaptive beamforming engine 405). The ultrasound image 1205 in FIG. 14 (*c*) is obtained as a comparative example, where the similarity operator 404 and the extraction converter 413 are removed from the first embodiment, and this image is obtained using only the adaptive beamforming engine and performing the averaging process in the time direction (the number of points for the averaging is identical to the decimation points for the case of the ultrasound image 1203). The ultrasound image 1206 in FIG. 14(*d*) is obtained by using only the adaptive beamforming engine, without performing the time-direction averaging.

FIG. 15(*a*) is obtained by profiling the brightness of the depth at which the maximum brightness points are positioned in the ultrasound images 1203 to 1206 of FIG. 14(*a*) to FIG. 14(*d*), along the channel direction, and FIG. 15(*b*) is obtained by profiling the brightness of the channel at which the maximum brightness points are positioned, along the depth direction. In FIG. 15(*a*) and FIG. 15(*b*), the brightness is displayed in decibels (dB).

As obvious from FIG. 14 and FIG. 15(*a*) and FIG. 15(*b*), the ultrasound image 1203 obtained in the first embodiment shows a sharp image of the point scatterers, being comparable to the ultrasound image 1206 obtained by calculating the adaptive weight, point by point. It is also found that the image of the point scatterer forms a smaller spot, relative to the ultrasound image 1205 obtained by calculating the adaptive weight in the time direction. If compared with the ultrasound image 1204 obtained by the delay-and-sum method, the image of the point scatterer becomes smaller by three times or more, and it is found that the resolution of the ultrasound image is drastically enhanced.

As described above, according to FIG. 14, FIG. 15(a) and FIG. 15(b), it has been confirmed that the present invention enhances the lateral resolution drastically, relative to the delay-and-sum method, and it is also possible to obtain performance comparable to other adaptive beamforming methods, and sharp point images with a small spot diameter.

In the aforementioned embodiment as described above, a result of the similarity computation is inputted into the adaptive beamforming engine, thereby making the point image in the time direction to be sharp with a small spot diameter, and further enabling acquisition of an ultrasound image including little false image and noise, in a stable manner and at a low cost. With this configuration, it is possible to implement an adaptive ultrasound imaging apparatus achieving both high image quality and high stability.

Seventh Embodiment

The ultrasound imaging apparatus according to the aforementioned second aspect the present invention will be specifically explained, as the seventh embodiment.

Figure 16:
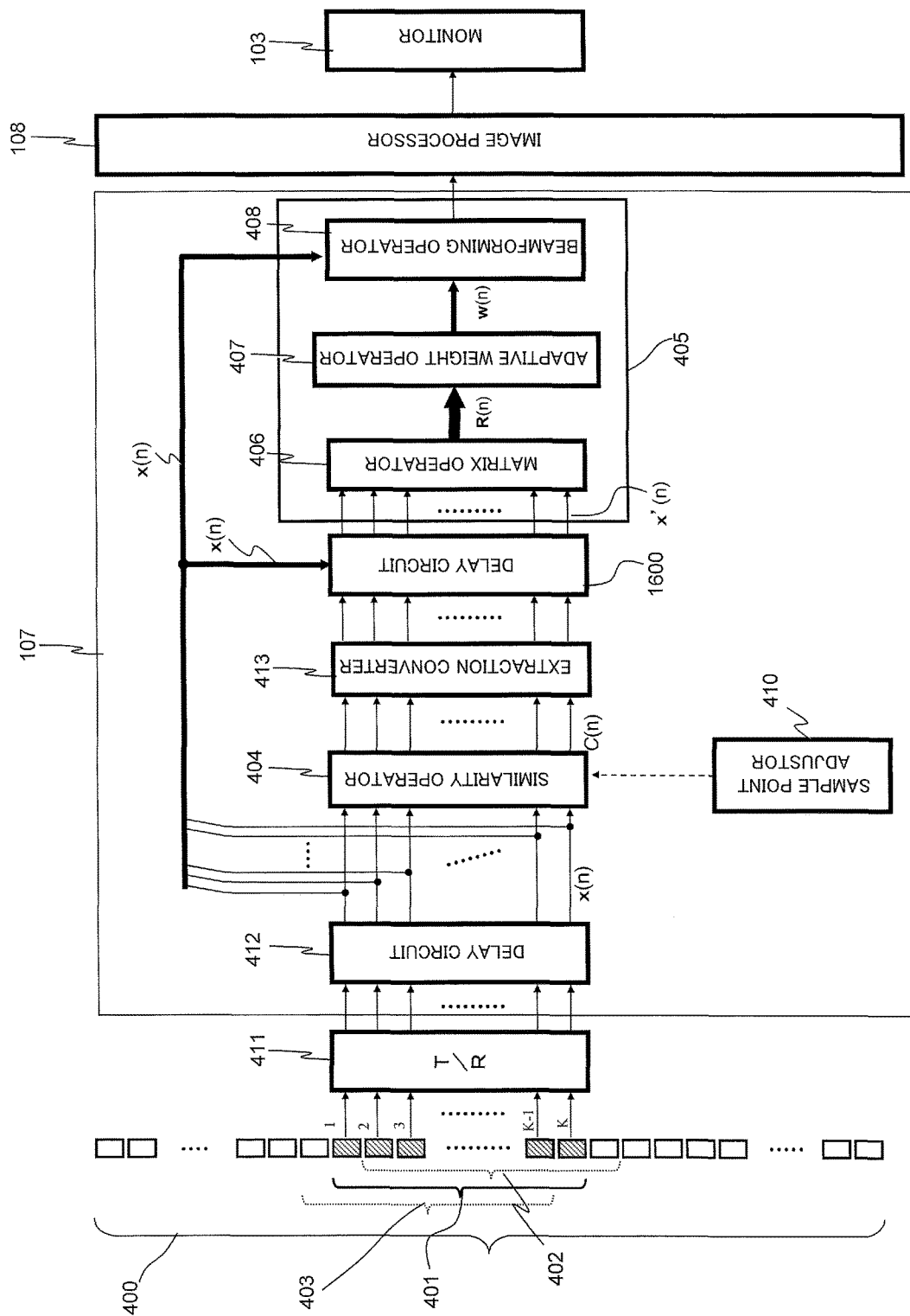
FIG. 16 is a block diagram illustrating a configuration of the receive beamformer according to the seventh embodiment.
Figure 17:
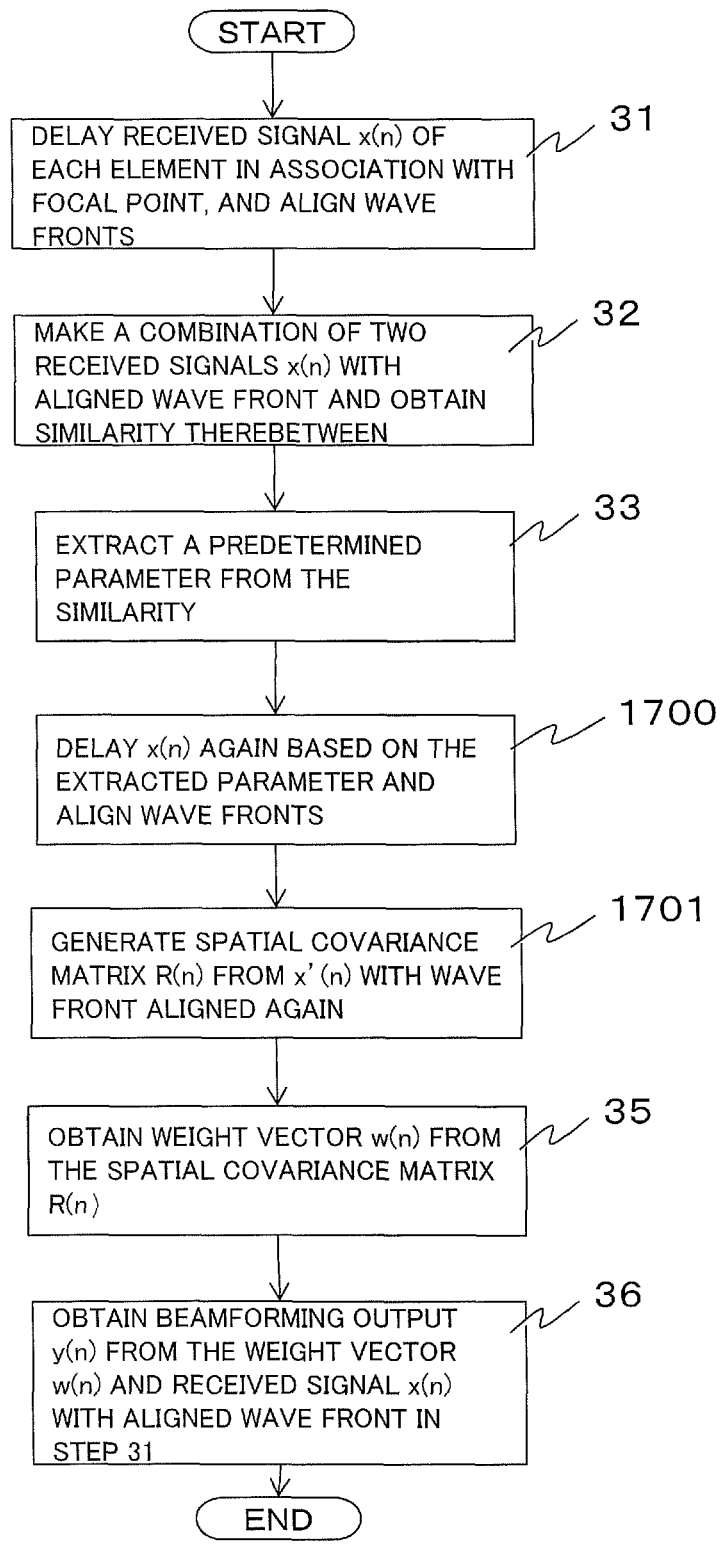
FIG. 17 is a flowchart showing the signal processing of the receive beamformer according to the seventh embodiment.

With reference to FIG. 16, the ultrasound imaging apparatus according to the seventh embodiment of the present invention will be explained. FIG. 16 is a block diagram illustrating the receive beamformer 107 according to the seventh embodiment. FIG. 17 is a flowchart showing the operations of each component in the receive beamformer 107.

As illustrated in FIG. 16, the receive beamformer 107 of the seventh embodiment is different in configuration from the receive beamformer 107 of the first embodiment as shown in FIG. 2, in the point that the second delay circuit 1600 is placed between the adaptive beamforming engine 405 and the extraction converter 413. In addition, as illustrated in FIG. 17, the steps 1700 and 1701 are added to the operations in the receive beamformer 107, instead of the step 34 in the flow of the first embodiment in FIG. 3. Since other configurations and operations are the same as those in the first embodiment, tedious explanation will not be provided.

In the seventh embodiment, as shown in FIG. 17, the received data x(n) is delayed again according to the similarity extraction value calculated based on the similarity in the extraction converter 413, thereby aligning the wave fronts (step 1700). The data x'(n) as to which the second delay circuit 1600 aligns the wave fronts again, is inputted into the adaptive beamforming engine 405, instead of the predetermined index being extracted ($a_p$, $\Delta t_p(n)$, $\phi_p(n)$, $\xi_p(n)$, and a combination of $I_p$ and $Q_p$ being the complex components indicated by the formula (8), and the like) in the first embodiment, and the spatial covariance matrix R(n) is generated (step 1701).

Specifically, as described in the first embodiment, the extraction converter 413 is allowed to extract time lag $\Delta t_p(n)$ from the reference time, by the cross correlation processing according to the formula (6). Here, the delay circuit 1600 makes use of the time lag $\Delta t_p$ to delay the received signal x(n) again, thereby aligning the wave fronts (step 1700). The data x'(n) in which the wave fronts are aligned by the delay circuit 1600 is expressed by the formula (24). Here, $\Delta \tau p(n)$ in the formula (24) represents the number of delayed sample points obtained by converting the scale of the lag $\Delta t_p(n)$ from the reference point of time, so as to be in tune with the sampling frequency of the received data. The formula (24) indicates an embodiment when the K-th channel is taken as the reference point, but any channel element from 1 to K may be applicable as the reference point.

[Formula 24]

$$x'_p(n) = x_p(n - \Delta \tau_p(n))$$

$$1 \leq p \leq K-1$$

$$x'_K(n) = x_K(n) \tag{24}$$

In the present embodiment, particularly as a preferred example, the formula (24) indicates the case where q=1 in the formula (3) and the formula (4). However, even when q is not equal to 1, the seventh embodiment is applicable by allowing the data to degenerate between the channels appropriately, such as resampling the received data in the channel direction.

The data x'(n) in which the wave fronts are aligned by the second delay circuit 1600 is inputted into the adaptive beamforming engine 405, and the matrix operator 406 calculates the spatial covariance matrix (step 1701). Therefore, in the seventh embodiment, the spatial covariance matrix R'(n) is expressed by the formula (25), and by using this spatial covariance matrix R'(n), the adaptive weight computation and the beamforming computation are performed. The subsequent configuration and a procedure for signal processing are the same as those in the first embodiment.

[Formula 25]

$$R'(n) = E[x'(n)x'^H(n)] \tag{25}$$

$$= E\left\{\begin{pmatrix} x'_1(n)x'^*_1(n) & x'_1(n)x'^*_2(n) & \cdots & x'_1(n)x'^*_k(n) \\ x'_2(n)x'^*_1(n) & x'_2(n)x'^*_2(n) & \cdots & x'_2(n)x'^*_k(n) \\ \vdots & \vdots & \ddots & \vdots \\ x'_K(n)x'^*_1(n) & x'_K(n)x'^*_2(n) & \cdots & x'_K(n)x'^*_K(n) \end{pmatrix}\right\}$$

$$= \frac{1}{N}\sum_{s=-S}^{S} x'(n-s)x'^H(n-s)$$

As described above, in the configuration of the seventh embodiment, it is possible to render the received data in phase, which are not sufficiently in phase by the delay circuit with a fixed parameter. As illustrated in FIG. 5(b), the lag $\Delta t_p$ indicates a difference of the arriving time points of the receive elements between the channels, and this difference corresponds to the time lag that occurs due to the influence from the wave front strain within the test subject. By using the received data x'(n) in which the wave fronts are aligned again, more accurate values may be used in estimating the channel weight in the adaptive beamforming engine.

Therefore, according to the present embodiment, the output from the second delay circuit 1600 in FIG. 16 is used as an input into the adaptive beamforming engine, thereby enhancing the degree of precision in estimating the channel weight in the adaptive beamforming engine.

EXPLANATION OF REFERENCES 100 test subject
101 ultrasound probe
102 ultrasound imaging apparatus
103 monitor
104 transmit beamformer
107 receive beamformer
108 image processor
130 console
201, 202, 203 one point in the space 205, 206, 207 delay concave form
208 received signal with aligned wave front
400 elements in array (ultrasound wave transducer)
401, 402, 403 active channel
404 similarity operator
405 sequential-type adaptive beamforming engine
406 matrix operator
407 adaptive weight operator
408 beamforming operator
410 sample point adjuster
411 transmit-receive separation circuit
412 delay circuit
413 extraction converter
501 LUT-type adaptive beamforming engine
502 weight estimator
503 weight memory
504 beamforming operator
601 controller
602 switch
701 subtraction part
703 weight changer
801, 802, 803 switching part
804, 805 switch
806 beamforming engine switching controller
808 switching timing controller
901 extraction parameter changer
902, 903 switching part
904 decimating operator
905 extraction operator
1000 wave front
1003 cross correlation window
1006 profile of normal received signal in the channel direction
1009 jump data in the profile
1010 profile of signal after cross correlation process in the channel direction
1011, 1015 period
1016 fixed phase
1101, 1102 tab with marks
1103 switch part
1104 a part of display area
1203 ultrasound image obtained in the first embodiment
1204 delay-and-sum type ultrasound image
1205 ultrasound image using only adaptive beamforming engine, with averaging in time direction
1206 ultrasound image using only adaptive beamforming engine without averaging in time direction
1600 second delay circuit

What is claimed is:

1. An ultrasound imaging apparatus comprising,
a plurality of elements that receive ultrasound signals from a test subject, wherein the ultrasound signals is delayed by a first delay;
a similarity operator that obtains a similarity between the received ultrasound signals of the plurality of elements;
a matrix operator that, using the similarity as in input, calculates a spatial covariance matrix R(n) that represents a covariance matrix at a certain sample point n in a time direction;
an adaptive weight operator that calculates an adaptive weight associated with the similarity by using the spatial covariance matrix R(n);
a beamforming operator that generates a beamforming output by using the adaptive weight and the received ultrasound signals;
an image processor that generates image data by using the beamforming output; and
an extractor, placed between the similarity operator and the adaptive weight operator, that extracts a predetermined index value indicating characteristics of the similarity;
a second delay part, placed between the plurality of elements and the similarity operator, that delays each of the received ultrasound signals that are received by the plurality of elements based on the predetermined index value extracted by the extractor so as to align wave fronts,
wherein the similarity operator obtains the similarity of the received ultrasound signals that are delayed by the delay part, and
wherein the adaptive weight operator uses the received ultrasound signals delayed by the delay part to obtain the adaptive weight.

2. The ultrasound imaging apparatus according to claim 1, wherein,
the similarity operator computes the similarity in the time direction.

3. The ultrasound imaging apparatus according to claim 1, wherein,
the adaptive weight operator uses the similarity obtained by the similarity operator to perform an adaptive signal processing, thereby obtaining the adaptive weight.

4. The ultrasound imaging apparatus according to claim 1, wherein,
the extractor is placed between the similarity operator and the adaptive weight operator, the extractor extracting the predetermined index value indicating characteristics of the similarity, and the adaptive weight operator uses the index value extracted by the extractor as the similarity.

5. The ultrasound imaging apparatus according to claim 3, wherein,
the adaptive weight operator generates the spatial covariance matrix from the similarity between the received signals, and performs the adaptive signal processing to obtain the adaptive weight.

6. The ultrasound imaging apparatus according to claim 1, wherein,
the multiple elements are placed side by side, and the similarity operator obtains the similarity between the received signals of two elements out of the multiple elements, one of the two elements being positioned a predetermined number of the elements away from the other element.

7. The ultrasound imaging apparatus according to claim 1, wherein,
if the number of the adaptive weights obtained by the adaptive weight operator is less than the number of the received signals, the beamforming operator performs computations to allow the multiple received signals to degenerate in accordance with the number of the adaptive weights, and generate a beamforming output by using the received signal after degeneration and the adaptive weight.

8. The ultrasound imaging apparatus according to claim 1, wherein,
the adaptive weight operator comprises,
a weight memory configured to store multiple-type combinations of a distribution of the similarity and a weight value, and
a weight estimator configured to select a combination of the distribution of the similarity and the weight value being stored in the weight memory, based on multiple distributions of the similarity received from the similarity operator, thereby enabling a selection from the weight values associated with the multiple distributions of the similarity received from the similarity operator.

9. The ultrasound imaging apparatus according to claim 1, wherein, the adaptive weight operator comprises a first operator and a second operator, wherein, the first operator uses the similarity obtained by the similarity operator to perform the adaptive signal processing, and computes the adaptive weight, and the second operator comprises, a weight memory configured to store in advance, multiple-type combinations of a distribution of the similarity and a weight value, and the weight estimator configured to select a combination of the distribution of the similarity and the weight value, being stored in the weight memory, based on multiple distributions of the similarity received from the similarity operator, and enabling a selection from the weight values associated with the multiple distributions of the similarity received from the similarity operator.

10. The ultrasound imaging apparatus according to claim 9, further comprising, a subtraction part configured to obtain a difference between a computation result of the first operator and a computation result of the second operator, and a weight changer configured to change the weight value stored in the weight memory of the second operator, according to the difference obtained by the subtraction part.

11. The ultrasound imaging apparatus according to claim 9, wherein, the adaptive weight operator comprises at least one of;

a drive switching part configured to selectively drive the first operator or the second operator, and an output switching part configured to selectively transfer to the image processor, an output from either of the first operator and the second operator.

12. The ultrasound imaging apparatus according to claim 11, further comprising, a timing controller configured to control switching timing of a drive switching part and an output switching part.

13. The ultrasound imaging apparatus according to claim 2, further comprising, a window-length adjuster configured to set any length of window in the time direction of the received signals, wherein, the similarity operator obtains the similarity between the received signals, as to the received signals within the window set by the window-length adjuster.

14. The ultrasound imaging apparatus according to claim 4, wherein, the similarity is a function, and the index value being predetermined indicating the characteristics of the similarity is at least one of; an amplitude, a phase, a complex number using the amplitude and the phase, only a real part of the complex value, and only an imaginary part of the complex value.

15. The ultrasound imaging apparatus according to claim 4, wherein, the extractor comprises an index switching part for switching and extracting as the index value indicating the characteristics of the similarity, at least any one of; an amplitude, a phase, a complex number using the amplitude and the phase, only a real part of the complex value, and only an imaginary part of the complex value.

16. The ultrasound imaging apparatus according to claim 1, wherein, the similarity operator comprises, a decimating operator configured to decimate the similarity being obtained in the time direction and output a result thereof.

* * * * *